United States Patent
Zhang et al.

(10) Patent No.: US 10,610,493 B2
(45) Date of Patent: Apr. 7, 2020

(54) DETOXIFICATION USING NANOPARTICLES

(71) Applicant: The Regents of the University of California, Oakland, CA (US)

(72) Inventors: Liangfang Zhang, San Diego, CA (US); Zhiqing Pang, Shanghai (CN); Ronnie H. Fang, San Diego, CA (US); Che-Ming Jack Hu, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/568,316

(22) PCT Filed: Apr. 13, 2016

(86) PCT No.: PCT/US2016/027250
§ 371 (c)(1),
(2) Date: Oct. 20, 2017

(87) PCT Pub. No.: WO2016/176041
PCT Pub. Date: Nov. 3, 2016

(65) Prior Publication Data
US 2018/0140558 A1    May 24, 2018

Related U.S. Application Data

(60) Provisional application No. 62/154,307, filed on Apr. 29, 2015.

(51) Int. Cl.
*A61K 9/51* (2006.01)
*A61K 9/50* (2006.01)
(Continued)

(52) U.S. Cl.
CPC .......... *A61K 9/5176* (2013.01); *A61K 9/5068* (2013.01); *A61K 45/06* (2013.01); *A61P 39/02* (2018.01); *Y10S 514/823* (2013.01)

(58) Field of Classification Search
None
See application file for complete search history.

(56) References Cited

U.S. PATENT DOCUMENTS 5,358,722 A    10/1994    Monzyk
5,491,219 A    2/1996    Mann
(Continued)

FOREIGN PATENT DOCUMENTS

CN    1798548 A    7/2006
CN    101306196 A    11/2008
(Continued)

OTHER PUBLICATIONS

R Fang "Cell Membrane-Coated Nanoparticles: Bridging Natural and Synthetic Nanomaterials for Novel Therapeutics"—PhD Thesis, University of California San Diego, 2014, pages: first page, pp. i-xxi and 1-204 (226 sheets). (Year: 2004).*

(Continued)

*Primary Examiner* — Isaac Shomer
(74) *Attorney, Agent, or Firm* — Eversheds Sutherland (US) LLP

(57) ABSTRACT

The present invention relates treatments of a toxin in a subject. The toxin at least partially effects its toxicity in the subject via binding to a target cell of the subject. The present invention provides for methods, combinations and pharmaceutical compositions for decreasing or neutralizing the effect of a toxin in a subject, using, inter alia, an effective amount of a nanoparticle comprising an inner core comprising a non-cellular material, and an outer surface comprising a cellular membrane derived from a source cell. Exemplary toxins include acetylcholinesterase (AChE) inhibitors such as organophosphate poisoning.

17 Claims, 4 Drawing Sheets

(51) Int. Cl.
*A61P 39/02* (2006.01)
*A61K 45/06* (2006.01)

(56) References Cited

U.S. PATENT DOCUMENTS

| | | | |
|---|---|---|---|
| 5,653,999 | A | 8/1997 | Gaudreault et al. |
| 6,506,381 | B1* | 1/2003 | Bitensky ............. A61K 9/5068 |
| | | | 424/93.73 |
| 8,846,026 | B2 | 9/2014 | Plebanski |
| 2004/0110695 | A1 | 6/2004 | Dobbie |
| 2004/0180094 | A1 | 9/2004 | Joyce |
| 2005/0118275 | A1 | 6/2005 | O'Hagan |
| 2006/0292174 | A1 | 12/2006 | de los Rios et al. |
| 2007/0243137 | A1 | 10/2007 | Hainfeld |
| 2007/0258889 | A1 | 11/2007 | Douglas et al. |
| 2009/0214663 | A1 | 8/2009 | Albrecht et al. |
| 2009/0218543 | A1 | 9/2009 | Hatton et al. |
| 2009/0274630 | A1 | 11/2009 | Huang |
| 2010/0021503 | A1 | 1/2010 | Denoel et al. |
| 2010/0028994 | A1 | 2/2010 | DeSimone |
| 2011/0280930 | A1 | 11/2011 | Batista et al. |
| 2013/0337066 | A1* | 12/2013 | Zhang ................. A61K 39/0011 |
| | | | 424/489 |
| 2014/0044647 | A1 | 2/2014 | Gho et al. |
| 2016/0136106 | A1 | 5/2016 | Zhang et al. |
| 2017/0000875 | A1 | 1/2017 | Hu |
| 2017/0079909 | A1 | 3/2017 | Zhang et al. |
| 2017/0095510 | A1 | 4/2017 | Lee |
| 2017/0274059 | A1 | 9/2017 | Zhang et al. |
| 2017/0367990 | A1 | 12/2017 | Lee |
| 2018/0085320 | A1 | 3/2018 | Zhang et al. |
| 2018/0140558 | A1 | 5/2018 | Zhang et al. |
| 2018/0153821 | A1 | 6/2018 | Zhang et al. |
| 2018/0169027 | A1 | 6/2018 | Zhang et al. |

FOREIGN PATENT DOCUMENTS

| | | |
|---|---|---|
| CN | 101735613 A | 6/2010 |
| GB | 2482069 A | 1/2012 |
| JP | 2005-525407 A | 8/2005 |
| RU | 2345805 C1 | 2/2009 |
| WO | 2005/020964 A1 | 3/2005 |
| WO | 2008/003524 A2 | 1/2008 |
| WO | 2008/013952 A1 | 1/2008 |
| WO | 2008/150276 A2 | 12/2008 |
| WO | 2010/070620 A1 | 6/2010 |
| WO | 2011/116219 A1 | 9/2011 |
| WO | 2013/052167 A2 | 4/2013 |
| WO | 2015/021390 A2 | 2/2015 |
| WO | 2015/187502 A1 | 12/2015 |
| WO | 2016/109306 A1 | 7/2016 |
| WO | 2017/087897 A1 | 5/2017 |

OTHER PUBLICATIONS

CMJ Hu, RH Fang, BT Luk, L Zhang. "Nanoparticle-detained toxins for safe and effective vaccination." Nature Nanotechnology, vol. 8, Dec. 2013, pp. 933-938. (Year: 2013).*
C-M J Hu, RH Fang, J Copp, BT Luk, L Zhang. "A biomimetic nanosponge that absorbs pore-forming toxins." Nature Nanotechnology, vol. 8, May 2013, pp. 336-340. (Year: 2013).*
PG Blain. "Organophosphorus poisoning (acute)." Clinical Evidence, 2011, 05:2102, pp. 1-17. (Year: 2011).*
PCT International Search Report and Written Opinion for PCT Application No. PCT/US2016/027250 dated Jul. 15, 2016 (8 pages).
Doctor et al., "Bioscavengers for the Protection of Humans Against Organophosphate Activity," Chemico-Biological Interactions, 2005, 167-171.
Moghimi et al., "Long-Circulating and Target-Specific Nanoparticles: Theory to Practice," Pharmacol Rev 2001, vol. 53, No. 2, pp. 283-318.
Davis et al., "Nanoparticle therapeutics: an emerging treatment modality for cancer." Nature Reviews/Drug Discovery 2008, vol. 7, pp. 71-782.
Peer et al., "Nanocarriers as an emerging platform for cancer therapy." Nature Nanotechnology 2007, vol. 2, pp. 751-760.
Yoo et al., "Factors that Control the Circulation Time of Nanoparticles in Blood: Challenges, Solutions and Future Prospects." Current Pharmaceutical Design 2010, vol. 16, pp. 2298-2307.
Geng et al., "Shape effects of filaments versus spherical particles in flow and drug delivery." Nature Nanotechnology 2007, vol. 2, pp. 249-255.
Alexis et al., "Factors Affecting the Clearance and Biodistribution of Polymeric Nanoparticles." Molecular Pharmaceutics 2008, vol. 5, No. 4, pp. 505-515.
Knop et al., "Poly(ethylene glycol) in Drug Delivery: Pros and Cons as Well as Potential Alernatives." Angew. Chem. Int. Ed. 2010, vol. 49, pp. 6288-6308.
Jiang et al., "Ultralow-Fouling, Functionalizable, and Hydrolyzable Zwitterionic Materials and Their Derivatives for Biological Applications." Adv. Mater 2010, vol. 22, pp. 920-932.
Yang et al., "Functionalizable and ultra stable nanoparticles coated with zwitterionic poly(carboxybetaine) in undiluted blood serum." Biomaterials 2009, vol. 30, pp. 5617-5621.
International Search Report and Written Opinion for PCT/US2012/039411, dated Apr. 8, 2013 (7 pages).
Tsai et al., "Self inhibition of phagocytosis: the affinity of 'marker of self' CD47 for SIRPalpha dictates potency of inhibition but only at low expression levels," Blood Cells Mol Dis 2010, 45:67-74.
Merkel et al., "Using mechanobiological mimicry of red blood cells to extend circulation times of hydrogel microparticles," Proc Natl Acad Sci U S A 2011, 108:586-591.
Desilets et al., "Nanoerythrosomes, a new derivative of erythrocyte ghost: IV. Fate of reinjected nanoerythrosomes," Anticancer Res 2001, 21:1741-1747.
Cheng et al., "Formulation of functionalized PLGA-PEG nanoparticles for in vivo targeted drug delivery," Biomaterials 2007, 28:869-876.
Tanaka, "Polymer-supported membranes as models of the cell surface," Nature 2005, 437:656-663.
Hochmuth et al., "Mechanical measurement of red cell membrane thickness," Science 1983, 220:101-102.
Fang et al., "Quick synthesis of lipid-polymer hybrid nanoparticles with low polydispersity using a single-step sonication method," Langmuir 2010, 26:16958-16962.
Popielarski et al., "A nanoparticle-based model delivery system to guide the rational design of gene delivery to the liver. 1. Synthesis and characterization," Bioconjug Chem 2005, 16:1063-1070.
Goutayer et al., "Tumor targeting of functionalized lipid nanoparticles: assessment by in vivo fluorescence imaging," Eur J Pharm Biopharm 2010, 75:137-147.
Xiao et al., "A self-assembling nanoparticle for paclitaxel delivery in ovarian cancer," Biomaterials 2009, 30:6006-6016.
Gratton et al., "Nanofabricated particles for engineered drug therapies: a preliminary biodistribution study of PRINT nanoparticles," J Control Release 2007, 121:10-18.
Peracchia et al., "Stealth PEGylated polycyanoacrylate nanoparticles for intravenous administration and splenic targeting," J Control Release 1999, 60:121-128.
Simberg, et al. "Biomimetic amplification of nanoparticle homing to tumors," Proc Natl Acad Sci U S A 2007, 104:932-936.
Oldenborg et al., "Role of CD47 as a marker of self on red blood cells," Science 2000, 288:2051-2054.
Avgoustakis et al., "Effect of copolymer composition on the physicochemical characteristics, in vitro stability, and biodistribution of PLGA-mPEG nanoparticles," Int J Pharm 2003, 259:115-127.
Zhang, L., "Lipid-polymer hybrid nanoparticles: synthesis, characterization and applications" Nano Life 2010, 1:163-173.
Sengupta et al., "Temporal targeting of tumor cells and neovasculature with a nanoscale delivery system," Nature 2005, 436:568-572.
Valencia et al., "Single-step assembly of homogenous lipid-polymeric and lipid-quantum dot nanoparticles enabled by microfluidic rapid mixing," ACS Nano 2010, 4:1671-1679.
Liu et al., "Porous nanoparticle supported lipid bilayers (protocells) as delivery vehicles," J Am Chem Soc 2009, 131:1354-1355.

(56) References Cited

OTHER PUBLICATIONS

Van Schooneveld et al., "Imaging and quantifying the morphology of an organic-inorganic nanoparticle at the sub-nanometre level," Nat Nanotechnol 2010, 5:538-544.
Dodge et al., "The preparation and chemical characteristics of hemoglobin-free ghosts of human erythrocytes," Arch Biochem Biophys 1963, 100:119-130.
Zhang, L. et al., "Self-assembled lipid-polymer hybrid nanoparticles: A robust drug delivery platform," ACS Nano 2008, 2:1696-1702.
Waugh et al., "Effects of lost surface area on red blood cells and red blood cell survival in mice," Am J Physiol 1996, 271:C1847-1852.
Arnold et al., "NanoCipro encapsulation in monodisperse large porous PLGA microparticles," J Control Release 2007, 121:100-109.
Jacobs et al., "An evaluation of antimalarial combinations against plasmodium berghei in the mouse," 1963 J Parasitol 49:920-925.
Lund et al., "Efficient isolation and quantitative proteomic analysis of cancer cell plasma membrane proteins for identification of metastasis-associated cell surface markers," J Proteome Res 2009, 8 (6), 3078-3090.
Graham, J. M., Isolation of membranes from tissue culture cells. Methods Mol Biol 1993, 19, 97-108.
Vayro et al., "Preparation and characterization of basolateral plasma-membrane vesicles from sheep parotid glands. Mechanisms of phosphate and D-glucose transport," Biochem J 1991, 279 (Pt. 3), 843-848.
Navas et al., "Isolation of purified plasma membranes from cultured cells and hepatomas by two-phase partition and preparative free-flow electrophoresis," Cancer Res 1989, 49 (8), 2147-2156.
Henon et al., "Isolation, identification and characterization of a plasma membrane preparation of guinea pig macrophages," C R Acad Sci Hebd Seances Acad Sci D 1977, 285(1), 121-122.
Boone et al., "Isolation of plasma membrane fragments from HeLa cells," J Cell Biol 1969, 41 (2), 378-392.
Petros et al., "Strategies in the design of nanoparticles for therapeutic applications." Nat. Rev. Drug Discov. 2010, 9 (8), 615-627.
Farokhzad et al., "Impact of Nanotechnology on Drug Delivery," ACS Nano 2009, 3(1), 16-20.
Chalmeau et al., "Alpha-Hemolysin pore formation into a supported phospholipid bilayer using cell-free expression," Biochim Biophys Acta 2011, 1808, 271.
Moorjani et al., "Nanoerythrosomes, a new derivative of erythrocyte ghost II: identification of the mechanism of action," Anticancer Res 1996, 16, 2831.
Vandana et al., "The role of the amino terminus in the kinetics and assembly of alpha-hemolysin of *Staphylococcus aureus*," J Biol Chem 1997, 272, 24858.
Valeva et al., Membrane Insertion of the Heptameric Staphylococcal a-Toxin Pore. J Biol Chem 2001, 276, 14835-1484.
Eaton, M., "Chemical Modification of Purified Diphtheria Toxin." The Journal of Immunology 1937 (33): 419-436.
International Search Report and Written Opinion for PCT/US2014/67688, dated Nov. 26, 2014 (8 pages).
Hu et al., "Erthrocyte Membrane-Camouflages Polymeric Nanoparticles as a Biomimetic Platform," PNAS 2011, 108 (27): 10980-10985.
Alexander et al., "Immunization of mice with pneumolysin toxoid confers a significant degree of protection against at least nine serotypes of *Streptococcus* pneumonia," Infect Immun 62, 5683 (Dec. 1994).
Andreeva-Kovalevskaya et al., "Pore-forming proteins and adaptation of living organisms to environmental conditions," Biochemistry (Mose) 73, 1473 (Dec. 2008).
Antonelli et al., "Encapsulation of Superparamagnetic Nanoparticles into Red Blood Cells as New Carriers of MRI Contrast Agents," Nanomedicine, 2011, 6(2):211-223.
Antonelli et al., "New Biomimetic Constructs for Improved In Vivo Circulation of Superparamagnetic Nanoparticles," Nanoscience and Nanotechnology, 2008, 8(5):2270-2278.

Aryal, et al., "Polymeric Nanoparticles with Precise Ratiometric Control over Drug Loading for Combination Therapy." Mol. Pharmaceutics, 2011, vol. 8, pp. 1401-1407, American Chemical Society.
Aryal et al., "Polymer—cisplalin conjugate nanoparticles for acid-responsive drug delivery," ACS Nano 4(1), 251-258 (2010).
Avgoustakis et al., "PLGA-mPEG nanoparticles of cisplalin: in vitro nanoparticle degradation, in vitro drug release and in Vivo drug residence in blood properties," J Control. Release 79(1-3), 123-135 (2002).
Beghini et al., "Anti-sera raised in rabbits against crotoxin and phospholipase A2 from Crotalus durissus cascavella venom neutralize the neurotoxicity of the venom and crotoxin," Toxicon 44, 141 (Aug. 2004).
Blum et al., "Pathways of Antigen Processing," Annu. Rev. Immunol., 2013, 31, pp. 443-473.
Boes et al., "Endosomal processing for antigen presentation mediated by CD1 and Class I major histocompatibility complex: roads to display or destruction," Immunology, 2009, 127(2), pp. 163-170.
Brahler et al., "Magnetite-Loaded Carrier Erythrocytes as Contrast Agents for Magnetic Resonance Imaging," American Chemical Society, Nano Letters, 2006, 6(11):2505-2509.
Branton et al., The potential and challenges of nanopore sequencing. Nat Biotechnol 26, 1146 (Oct. 2008).
Budhian et al., "Controlling the in vitro release profiles for a system of haloperidol-loaded PLGA nanoparticles," Int. J. Pharm. 346(1-2), 151-159 (2008).
Ce et al., "Pharmacokinetics of Morphine Loaded into Erythrocyte in Rabbits," Journal of China Pharmaceutical University, 2006, 37(2):150-152.
Chen et al., "Potent neutralization of anthrax edema toxin by a humanized monoclonal antibody that competes with calmodulin for edema factor binding," Proc Nall Acad Sci USA 106, 13487 (Aug. 11, 2009).
Cho et al., "A Multifunctional Core-Shell Nanoparticle for Dendritic Cell-Based Cancer Immunotherapy," Nature Nanotechnology: 6, 675-82 (2011).
Clatworthy et al., "Targeting virulence: a new paradigm for anti-microbial therapy," Nat Chem Biol 3, 541 (Sep. 2007).
Cryz, Jr. et al., "Effect of Chemical and Heat Inactivation on the Antigenicity and Immunogenicity of Vibrio Cholerae," Infect. Immun., 1982, 38(1), pp. 21-26.
Doshi et al., "Red Blood Cell-Mimicking Synthetic Biomaterial Particles," PNAS, 2009, 106(51):21495-21499.
Edelson et al., "Intracellular antibody neutralizes Listeria growth," Immunity 14, 503 (May 2001).
Edelson et al., "Cutting edge: paradigm revisited: antibody provides resistance to Listeria infection," J. Immunol. 163, 4087 (Oct. 15, 1999).
European Search Report for EP Application No. 12838792.5, dated May 7, 2015 (5 pages).
European Supplementary Search Report for EP Application No. 12838792.5, dated May 27, 2015 (4 pages).
Gao et al., "pH-Responsive Nanoparticles for Drug Delivery," Mol. Pharm. 7(6), 1913-1920 (2010).
Gilbert et al., "Pore-forming toxins," Cell Mol. Life Sci. 59, 832 (May 2002).
Goshi et al., "Studies on the Pathogenesis of Staphylococcal Infection." The Journal of Experimental Medicine. 1961, 113(2): 259-270.
Greenberg et al., "Phase I dose finding studies of an adjuvanted Clostridium difficile toxoid vaccine," Vaccine, 2012, 30, pp. 2245-2249.
Gu et al., "Precise engineering of targeted nanoparticles by using self-assembled biointegraled block copolymers,"Proc. Nall. Acad. Sci. USA 105(7), 2586-2591 (2008).
Hamidi et al., "Encapsulation of Valproate-Loaded Hydrogel Nanoparticles in Intact Human Erthrocytes: A Novel Nano-Cell Composite for Drug Delivery," Journal of Pharmaceutical Sciences, 2011, 100(5):1702-1711.
Harush-Frenkel et al., "Targeting of nanoparticles to the clathrin—mediated endocytic pathway," Biochem. Biophys. Res. Commun., 2007, 353, pp. 26-32.

(56) References Cited

OTHER PUBLICATIONS

Higuchi, T. Rate of release of medicaments from ointment bases containing drugs in suspension. J. Pharm. Sci. 50, 874-875 (1961).
Holmgren et al., "Development of improved cholera vaccine based on subunit toxoid," Nature, 1977, 269, pp. 502-604.
Hoshino et al., "The rational design of a synthetic polymer nanoparticle that neutralizes a toxic peptide in vivo," Proc Nall Acad Sci USA 109, 33 (Jan. 3, 2012).
Hoshino et al., "Recognition, neutralization, and clearance of target peptides in the bloodstream of living mice by molecularly imprinted polymer nanoparticles: a plastic antibody," J. Am. Chem. Soc. 132, 6644 (May 19, 2010).
Hu et al., "Therapeutic Nanoparticles to Combat Cancer Drug Resistance," Curr. Drug Metab. 10(8), 836-841 (2009).
Hu et al., "Erthrocyte-Inspired Delivery Systems," Adv. Healthcare Mater., 2012, 1:537-547.
Hung et al., "Small-molecule inhibitor of Vibrio cholerae virulence and intestinal colonization," Science 310, 670 (Oct. 28, 2005).
Huwyler et al., "By-passing of P-glycoprotein using Immunoliposomes," J. Drug Target. 10(1), 73-79 (2002).
Kirkham et al., "Construction and immunological characterization of a novel nontoxic protective pneumolysin mutant for use in future pneumococcal vaccines," Infect Immun 74, 586 (Jan. 2006).
Kitchin, N., "Review of diphtheria, tetanus and pertussis vaccines in clinical development," Expert Rev. Vaccines, 2011, 10(5), pp. 605-615.
Klainer et al., "Staphylococcal Alpha-Hemolysin: Detection on the Erythrocyte Membrane by Immunofluorescence," Science, vol. 145, No. 3633, pp. 714-715 (Aug. 14, 1964).
Kum et al., "Inhibition of staphylococcal enterotoxin A—induced superantigenic and lethal activities by a monoclonal antibody to toxic shock syndrome toxin-1," J Infect Dis 183, 1739 (Jun. 15, 2001).
Li et al., "Alpha-Alumina Nanoparticles Induce Efficient Autophagy—Dependent Cross-Presentation and Potent Antitumour Response," Nature Nanotechnology 6, 645-650 (2011).
Li et al., "The effect of pH on the polymer degradation and drug release from PLGA-mPEG microparticles", J. Appl. Polym. Sci. 109(1), 475-482 (2008).
Lowenberg et al. High-Dose Daunorubicin in Older Patients with Acute Myeloid Leukemia. New Engl. J. Med. 361 (13), 1235-1248 (2009).
Ma et al., "Vesicular polydiacetylene sensor for colorimetric signaling of bacterial pore-forming toxin," Langmuir 21, 6123 (Jul. 5, 2005).
Markov et al., "Human Erythrocytes as Nanoparticle Carriers for Magnetic Particle Imaging," Physics in Medicine and Biology, 2010, 55(21):6461-6473.
McCormick et al., "Chemical inhibition of alpha-toxin, a key corneal virulence factor of *Staphylococcus aureus*," Invest Ophthalmol Vis Sci, 50, 2848 (Jun. 2009).
Metz et akl., "Identification of Formaldehyde-induced Modifications in Proteins: Reactions with Model Peptides," J. Biol. Chem., 2004, 279(8), pp. 6235-6243.
Xu, Experimental Study on Magnetized Technique of Doxorubicin-loaded Erythrocytes, Wanfang Data, pp. 13, 21-22, 35, 52, Oct. 19, 2009.
Moon et al., "Interbilayer-Crosslinked Multilamellar Vesicles as Synthetic Vaccines for Potent Humoral and Cellular Immune Responses," Nature Materials 10.3 (2011): 243-251.
Moore et al., "Specific Targeting and Delivery of Virus Envelope—Coated Nanoparticle Cargoes into Receptor-Bearing Cells and Subcellular Compartments," NSTI-Nanotech 2007, vol. 2, pp. 370-373.
Mortimer, E.A. Jr., "Immunization Against Infectious Disease," Science, 1978, 200, pp. 902-907.
Nakouzi et al., "Passive administration of monoclonal antibodies to anthrolysin 0 prolong survival in mice lethally infected with Bacillus anthracis," BMC Microbial 8, 159 (2008).
O'Hanley et al., "Alpha-hemolysin contributes to the pathogenicity of piliated digalactoside—binding *Escherichia coli* in the kidney: efficacy of an alpha-hemolysin vaccine in preventing renal injury in the BALB/c mouse model of pyelonephritis," Infect Immun. 59, 1153 (Mar. 1991).
Parish et al., "Staphylococcal Infection: Antitoxic Immunity," Br. Med. J., 1960, 1(5175), pp. 743-747.
Petrov et al., "Toxicity and Immunogenicity of Neisseria meningitidis Lipopolysaccharide Incorporated into Liposomes," Infect. Immun. 1992, 60(9), pp. 3897-3903.
Pitt et al., "The kinetics of drug cleavage and release from matrices containing covalent polymer—drug conjugates," J. Control. Release 33(3), 391-395 (1995).
Pornpattananangkul et al., Bacterial Toxin-Triggered Drug Release from Gold Nanoparticle—Stabilized Liposomes for the Treatment of Bacterial Infection. J_ Am. Chem. Soc. 133(11 ), 4132-4139 (2011 ).
Ragle et al., "Anti-Alpha-Hemolysin Monoclonal Antibodies Mediate Protection against *Staphylococcus aureus* Pneumonia," Infection and Immunity. 2009, 77(7):2712-2718.
Rapoport et al., "Intracellular uptake and trafficking of pluronic micelles in drug-sensitive and MOR cells: Effect on the intracellular drug localization," J. Pharm. Sci. 91(1), 157-170 (2002).
Rosado et al., "The MACPF/CDC family of pore-forming toxins," Cell Microbiol 10, 1765 (Sep. 2008).
Sahoo et al., Enhanced anti proliferative activity of transferrin—conjugated paclitaxel-loaded nanoparticle, is mediated via sustained intracellular drug retention. Mol. Pharm. 2(5), 373-383 (2005).
Schmitt et al., "Bacterial toxins: friends or foes?," Emerg. Infect. Dis., 1999, 5(2), pp. 224-234.
Shoham et al. "Antivirulence agents against MRSA," Future Med Chem, 3, 775 (May 2011).
Siepmann, et al., "Higuchi equation: derivation, applications, use and misuse," Int. J. Pharm. 418(1), 6-12 (2011).
Takae et al., "PEG-detachable polyplex micelles based on disulfide-linked block catiomers as bioresponsive nonviral gene vectors," J Am. Chem. Soc. 130(18), 6001-6009 (2008).
Tong et al., "Ring-opening polymerization—mediated controlled formulation of polylaclide-drug nanoparticles," J. Am. Chem. Soc. 131(13), 4744-4754 (2009).
Tong et al., "Controlled Synthesis of Camptothecin—Polylaclide Conjugates and Nanoconjugates," Bioconjug. Chem. 21(1), 111-121 (2010).
Tongchusak et al., "Induction of Anti-Tumor Cytotoxic T Cell Responses Through PLGA—Nanoparticle Mediated Antigen Delivery," Biomaterials (2011), 32(14):3666-78.
Wardenburg et al., "Vaccine protection against *Staphylococcus aureus* pneumonia," The Journal of Experimental Medicine. 2008, 205(2): 287-294.
Watts et al., "Pathways of antigen processing and presentation," Rev. Immunogenel. 1999, 1, pp. 60-74.
Yoo et al., "In vitro and in vivo anti-tumor activities of nanoparticles based on doxorubicin—PLGA conjugates," Journal of Controlled release 2000, 68 (3): 419-431.
Zhang et al., "Size-Dependent Endocytosis of Nanoparticles," Adv. Maier., 2009, 21, pp. 419-424.
Zhang et al., "Transmembrane Delivery of Aggregated [Gd@C82(0h)22]n Nanoparticles," Journal of Nanoscience and Nanotechnology, 2010, 10(12):8556-8561.
Zhao et al., "Interaction of Mesoporous Silica Nanoparticles with Human Red Blood Cell Membranes: Size and Surface Effects," ACS Nano, 2011, 5(2):1366-1375.
Chinese Office Action for CN Application No. 201280035048.5, dated Nov. 10, 2015 (13 pages).
Chinese Office Action, dated Feb. 2, 2015.
Japanese Office Action for JP Application No. 2014-513590 dated Feb. 19, 2016 (9 pages).
International Preliminary Report on Patentability for PCT Application No. PCT/US2012/039411 dated Apr. 3, 2014 (6 pages).
International Preliminary Report on Patentability for PCT/US2014/067688, dated Jun. 7, 2016.
International Search Report and Written Opinion for PCT/US2014/067688, dated Feb. 4, 2015.
Office Action issued in U.S. Appl. No. 15/100,273, dated Nov. 18, 2016.

(56) References Cited

OTHER PUBLICATIONS

Office Action issued in U.S. Appl. No. 15/100,273, dated Feb. 17, 2017.
Response as filed on Nov. 24, 2015 with the European Patent Office in response to the European Supplementary Search Report for EP Application No. 12838792.5, dated May 27, 2015 (9 pages).
Response to Chinese Office Action for CN Application No. 2012800350485, filed on Jan. 25, 2016 (63 pages).
Response to Office Action for CN Application No. 2012800350485, filed on Jul. 6, 2015 and English version of remarks and claims.
Response to Restriction Requirement issued in U.S. Appl. No. 15/100,273, filed Jan. 18, 2017.
Response to Taiwanese Office Action for TW Application No. 101119113, filed on Feb. 5, 2016 (56 pages).
Response to Taiwanese Office Action in TW Application No. 101119113 submitted on Jun. 21, 2018 (8 pages).
Taiwanese Office Action for TW Application No. 101119113 dated Jun. 7, 2016 (13 pages with English translation).
Taiwanese Office Action for TW Application No. 101119113 dated Oct. 6, 2015 (15 pages).
Ming et al., "Erythrocyte Membrane—Camouflaged Polymeric Nanoparticles as a Biomimetic Delivery Platform," PNAS, 2011, 108(27):10980-10985.

\* cited by examiner

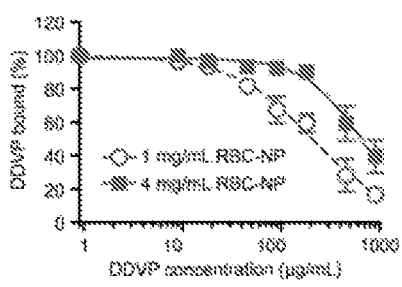
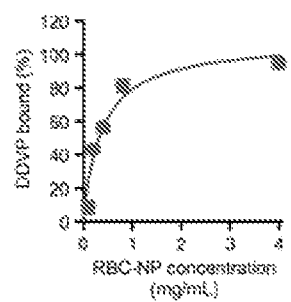
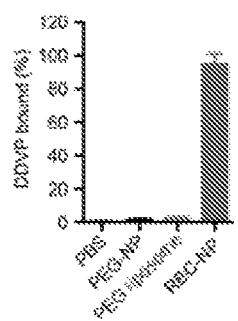
FIGURE 3A                FIGURE 3B                FIGURE 3C
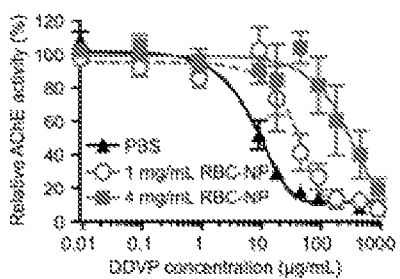
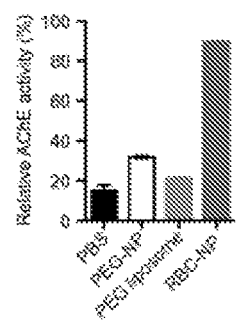
FIGURE 3D                FIGURE 3E

DETOXIFICATION USING NANOPARTICLES

CROSS REFERENCE TO RELATED APPLICATIONS

This application claims the priority benefit of PCT/US2016/027250 filed on Apr. 13, 2016 which claims priority to U.S. Provisional Patent Application No. 62/154,307, filed Apr. 29, 2015. The entire contents of which are hereby incorporated by reference.

STATEMENT REGARDING FEDERALLY SPONSORED RESEARCH

This invention was made with Government support under HDTRA1-14-1-0064 awarded by the Defense Threat Reduction Agency and under DK095168 awarded by the National Institutes of Health. The government has certain rights in the invention.

FIELD OF THE INVENTION

The present invention relates to treatments of a toxin in a subject. The toxin at least partially effects its toxicity in the subject via binding to a target cell of the subject. The present invention provides for methods, combinations and pharmaceutical compositions for decreasing or neutralizing the effect of a toxin in a subject, using, inter alia, an effective amount of a nanoparticle comprising an inner core comprising a non-cellular material, and an outer surface comprising a cellular membrane derived from a source cell. Exemplary toxins include acetylcholinesterase (AChE) inhibitors such as organophosphate poisoning.

BACKGROUND OF THE INVENTION

Organophosphate poisoning is caused by exposure to organophosphorus compounds (OPs), which irreversibly inactivate acetylcholinesterase (AChE) by phosphorylating the serine hydroxyl residue on AChE and lead to the accumulation of acetylcholine (ACh) in the body. Such accumulation disrupts cholinergic synaptic transmissions and can lead to various neurotoxic effects, including death in severe cases. OPs are one of the most common causes of poisoning worldwide and are frequently used in suicide attempts. There is an estimated 750,000 to 3 million global cases of OP poisonings per year with hundreds of thousands of annual fatalities (1, 2). Because of their strong toxicity to humans, many OPs are applied in chemical warfare, serving as the primary ingredients in multiple nerve agents including sarin, tabun, soman, and VX. Typically, these nerve agents take effect within 1-10 min of exposure and can cause acute lethality within 15-30 min (3). Combined with their ease of production, highly toxic OPs represent a great threat to both military and civilian populations (4). Effective treatment of OP poisoning is of significant value to public health.

Removal of OPs from the body is difficult because they can easily enter circulation via several routes, including inhalation, ingestion, and dermal absorption. Current antidotes for OP poisoning consist of a pretreatment with carbamates to protect AChE from inhibition by OP compounds and post-exposure treatments with anti-cholinergic drugs (5), which serve to counteract the effects of excess ACh. Atropine are the most widely used antidote against OP poisoning in conjunction with pralidoxime or other pyridinium oximes (such as trimedoxime and obidoxime) for AChE reactivation (6). However, these treatments are associated with serious side effects and can be difficult to administer. Recent meta-analyses indicate that the use of "-oximes" appears to be of no benefit and can potentially be detrimental (7, 8). In addition, it can be difficult to achieve a sufficient level of atropinization (9), as a high dose of the muscarinic antagonist is needed to block the action of over accumulated peripheral ACh following AChE inactivation. Enzyme bioscavengers such as human serum butyrylcholinesterase (BChE) and human paraoxonase 1 (PON1) have been explored as treatment options to react and hydrolyze OPs before they can reach their physiological targets (10-12). However, large-scale production of these recombinant proteins remains a hurdle in their translation (13). Clinical treatment of OP poisoning may thus benefit from alternative strategies that can effectively deactivate the compounds in the bloodstream.

New methods and compositions for decreasing or neutralizing the effect of a toxin, e.g., organophosphate poisoning, in a subject are needed. The present disclosure addresses this and the related needs in the art.

SUMMARY OF THE INVENTION

In one aspect, the present invention provides for a method for decreasing or neutralizing the effect of a toxin in a subject, which method comprises administering, to a subject in need, or to cells of said subject, an effective amount of a nanoparticle comprising a) an inner core comprising a non-cellular material, and b) an outer surface comprising a cellular membrane derived from a source cell, wherein said toxin at least partially effects its toxicity in said subject via binding to a target cell of said subject, and 1) said source cell and said target cell are two different types of cells; or 2) said toxin is an acetylcholinesterase (AchE) inhibitor, and preferably, said source cell is selected from the group consisting of a blood cell, an endothelial cell, an epithelial cell, a neuronal cell, a cardiac cell and a muscle cell.

In another aspect, the present invention is directed to an use of an effective amount of a nanoparticle for the manufacture of a medicament for decreasing or neutralizing the effect of a toxin in a subject, wherein said nanoparticle comprises: a) an inner core comprising a non-cellular material, and b) an outer surface comprising a cellular membrane derived from a source cell, said toxin at least partially effects its toxicity in said subject via binding to a target cell of said subject, and 1) said source cell and said target cell are two different types of cells; or 2) said toxin is an acetylcholinesterase (AchE) inhibitor, and said source cell is selected from the group consisting of a blood cell, an endothelial cell, an epithelial cell, a neuronal cell, and a cardiac cell.

In still another aspect, the present invention provides for a combination for decreasing or neutralizing the effect of a toxin in a subject, which combination comprises an effective amount of a nanoparticle and an effective amount of a second prophylactic or therapeutic agent for decreasing or neutralizing the effect of a toxin in a subject, wherein said nanoparticle comprises: a) an inner core comprising a non-cellular material, and b) an outer surface comprising a cellular membrane derived from a source cell, said toxin at least partially effects its toxicity in said subject via binding to a target cell of said subject, and 1) said source cell and said target cell are two different types of cells; or 2) said toxin is an acetylcholinesterase (AchE) inhibitor, and said source cell is selected from the group consisting of a blood cell, an endothelial cell, an epithelial cell, a neuronal cell, and a cardiac cell. The present invention also provides for a pharmaceutical composition comprising the combination and a method for using the combination or the pharmaceutical composition comprising the combination.

In some aspects, the prevent disclosure relates to U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011. The contents of the above applications are incorporated by reference in their entireties.

BRIEF DESCRIPTION OF THE DRAWINGS

FIGS. 3A-3E. In vitro neutralization of DDVP by RBC-NPs. (3A) DDVP removal by different amounts of RBC-NPs was analyzed by titrating the concentration of DDVP in the reaction mixtures. (3B) Kinetics of DDVP absorption and removal were investigated by incubating DDVP with different concentrations of RBC-NPs for 30 min. (3C) DDVP absorption and removal by different nanoformulations (PEG-NPs, PEG liposomes, and RBC-NPs) were analyzed by incubating DDVP with the respective nanoformulations for 30 min. (3D) RBC ghost AChE activity in the presence of different concentrations of RBC-NPs following incubation with varying levels of DDVP for 30 min. Higher RBC-NP content conferred higher in vitro anti-OP effect. (3E) RBC ghost AChE activity in the presence of different nanoformulations (PEG-NPs, PEG liposomes, and RBC-NPs) following incubation with DDVP for 30 min. Co-incubation with RBC-NPs resulted in the highest AChE activity retention on the RBC ghosts. All error bars represent standard error of mean.

DETAILED DESCRIPTION OF THE INVENTION

Figure 1:
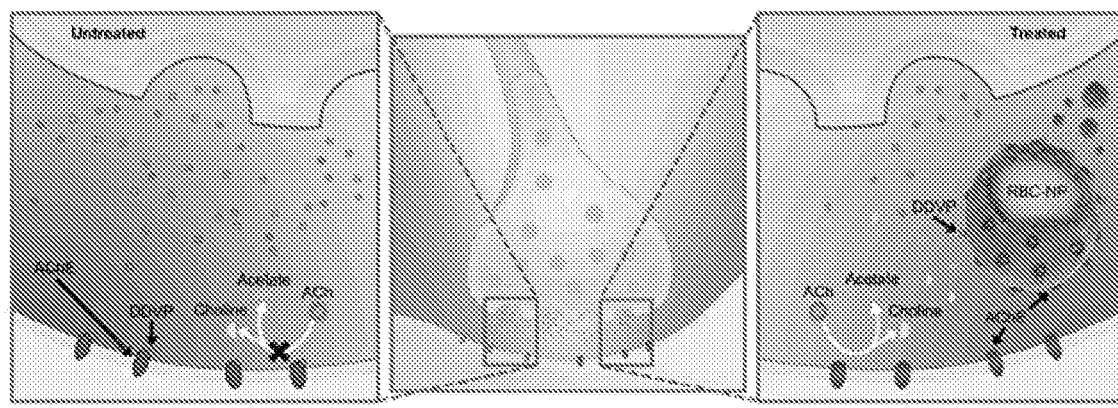
FIG. 1. Schematic of RBC-NPs as anti-OP bioscavengers for treating OP poisoning. With no treatment (left), dichlorvos (DDVP), a model OP, irreversibly binds acetylcholinesterase (AChE), preventing the breakdown of acetylcholine (ACh) into choline and acetate. When RBC-NPs are introduced (right), they scavenge free DDVP molecules, preserving the ability of endogenous AChE to perform the function of breaking down Ach.

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, *Molecular Cloning: A Laboratory Manual*, $2^{nd}$ ed. (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and Remington, *The Science and Practice of Pharmacy*, $20^{th}$ ed., (Lippincott, Williams & Wilkins 2003).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: The term "nanoparticle" as used herein refers to nanostructure, particles, vesicles, or fragments thereof having at least one dimension (e.g., height, length, width, or diameter) of between about 1 nm and about 10 µm. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting an inner core covered by an outer surface comprising the membrane as discussed herein. The invention contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20''' ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (PIP3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Methods for Decreasing or Neutralizing the Effect of a Toxin in a Subject In one aspect, the present invention provides for a method for decreasing or neutralizing the effect of a toxin in a subject, which method comprises administering, to a subject in need, or to cells of said subject, an effective amount of a nanoparticle comprising a) an inner core comprising a non-cellular material, and b) an outer surface comprising a cellular membrane derived from a source cell, wherein said toxin at least partially effects its toxicity in said subject via binding to a target cell of said subject, and 1) said source cell and said target cell are two different types of cells; or 2) said toxin is an acetylcholinesterase (AchE) inhibitor, and preferably, said source cell is selected from the group consisting of a blood cell, an endothelial cell, an epithelial cell, a neuronal cell, a cardiac cell and a muscle cell. In some embodiments, the toxin is not a toxin disclosed in U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011.

The present methods can be used to decrease or neutralize the effect of a toxin in any suitable subject. In some embodiments, the subject is a mammal. In some embodiments, the mammal is a human. In other embodiments, the mammal is a non-human mammal, including a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

In some embodiments, the present methods can be used for decreasing the effect of a toxin in a subject. In other embodiments, the present methods can be used for neutralizing the effect of a toxin in a subject. The present methods can be used to decrease or neutralize the effect of a toxin in a subject to any suitable degree. For example, present methods can be used to decrease or neutralize the effect of a toxin in a subject by at least 10%, 20%, 30%, 40%, 50%, 60%, 70%, 80%, 90%, 91%, 92%, 93%, 94%, 95%, 96%, 97%, 98%, 99% or more compared to a comparable untreated subject or to the same subject at an untreated stage.

The nanoparticle used in the present methods can comprise any suitable inner core. For example, the inner core of the nanoparticle can comprise a polymeric particle core, a silica particle core, or a metal, e.g., gold, particle core. Any suitable polymeric particle core can be used. In some embodiments, the polymeric particle core can comprise an optical shift property. In other embodiments, the polymeric particle core can comprise a metal, e.g., gold, iron oxide or a quantum dot. In still other embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In yet other embodiments, the inner core of the nanoparticle supports the outer surface.

The nanoparticle used in the present methods can comprise a cellular membrane derived from any suitable source cell. For example, the nanoparticle can comprise a plasma membrane or an intracellular membrane derived from any suitable source cell. In some embodiments, the nanoparticle can comprise an intracellular membrane derived from any suitable source cell e.g., a blood cell such as a red blood cell, a white blood cell, a platelet, or a macrophage, an endothelial cell, an epithelial cell, a neuronal cell, or a cardiac cell. In other embodiments, the nanoparticle can comprise a plasma membrane derived from any suitable source cell, e.g., a blood cell such as a red blood cell, a white blood cell, a platelet, or a macrophage, an endothelial cell, an epithelial cell, a neuronal cell, or a cardiac cell.

The therapeutic agent, the prophylactic agent, the diagnostic or marker agent, the prognostic agent, the isolation agent, the monitoring agent, or a combination thereof, can be comprised in any suitable location in the composition used in the present methods. For example, the therapeutic agent, the prophylactic agent, the diagnostic or marker agent, the prognostic agent, the isolation agent, the monitoring agent, or a combination thereof, can be comprised in the nanoparticle. In some embodiments, the therapeutic agent, the prophylactic agent, the diagnostic or marker agent, the prognostic agent, the isolation agent, the monitoring agent, or a combination thereof, can be comprised in a releasable cargo in the nanoparticle. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle. The nanoparticle can comprise any suitable type of a releasable cargo. For example, the releasable cargo can be a metallic particle, a polymeric particle, a dendrimer particle, or an inorganic particle. In some embodiments, the therapeutic agent, the prophylactic agent, the diagnostic or marker agent, the prognostic agent, the isolation agent, the monitoring agent, or a combination thereof, can be comprised in the composition used in the present methods but outside the nanoparticle. In other embodiments, the therapeutic agent, the prophylactic agent, the diagnostic or marker agent, the prognostic agent, the isolation agent, the monitoring agent, or a combination thereof, can be administered to the subject separately from the composition used in the present methods. The composition used in the present methods and the additional substance can be administered to the subject simultaneously or sequentially.

The nanoparticle used in the present methods can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm, or any sub-range within about 10 nm to about 10 µm, e.g., any range between any two of the above sizes.

The nanoparticle used in the present methods can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle used in the present methods substantially lacks constituents of the source cell, e.g., a blood cell such as a red blood cell, a white blood cell, a platelet, or a macrophage, an endothelial cell, an epithelial cell, a neuronal cell, or a cardiac cell, from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the source cell, e.g., a blood cell such as a red blood cell, a white blood cell, a platelet, or a macrophage, an endothelial cell, an epithelial cell, a neuronal cell, or a cardiac cell, from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle used in the present methods substantially maintains natural structural integrity or activity of the cellular membrane derived from a source cell or the constituents of the cellular membrane derived from a source cell so that the nanoparticle functions as decoy for the toxin's target cell, e.g., neuronal cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for functioning as decoy for the toxin's target cell, e.g., neuronal cells.

In some embodiments, the nanoparticle used in the present methods is biocompatible or biodegradable. For example, the inner core of the nanoparticle comprises PLGA and the outer surface of the nanoparticle comprises a plasma membrane derived from a source cell, e.g., a blood cell such as a red blood cell, a white blood cell, a platelet, or a macrophage, an endothelial cell, an epithelial cell, a neuronal cell, or a cardiac cell.

The nanoparticle used in the present methods can have any suitable half-life in vivo. For example, the nanoparticle can have a half-life in blood circulation in vivo for at least about 2-5 times of the half-life of a PEG-coated, comparable nanoparticle, or has a half-life in blood circulation in vivo for at least about 1 to about 40 hours, e.g., about 1, 2, 3, 4, 5, 6, 7, 8, 9, 10, 15, 20, 25, 30, 35 or 40 hours.

The outer surface of the nanoparticle used in the present methods can further comprise a synthetic membrane. In some embodiments, the nanoparticles used in the present methods comprise a mixture of nanoparticles that comprise an outer surface comprising a cellular membrane and nanoparticles that comprise an outer surface comprising a synthetic membrane. The nanoparticles that comprise an outer surface comprising a synthetic membrane may or may not absorb or bind to a toxin. In some embodiments, both the nanoparticles that comprise an outer surface comprising a cellular membrane and nanoparticles that comprise an outer surface comprising a synthetic membrane absorb or bind to a toxin. In other embodiments, the nanoparticles that comprise an outer surface comprising a cellular membrane absorb or bind to a toxin, but the nanoparticles that comprise an outer surface comprising a synthetic membrane do not absorb or bind to a toxin.

The composition used in the present methods can comprise the nanoparticles that comprise an outer surface comprising a cellular membrane and nanoparticles that comprise an outer surface comprising a synthetic membrane in any suitable ratio. In some embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a cellular membrane. In other embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a synthetic membrane. For example, the composition used in the present methods can comprise about 1-10% (w/w) of the nanoparticles that comprise an outer surface comprising a cellular membrane and about 90-99% (w/w) of the nanoparticles that comprise an outer surface comprising a synthetic membrane, about 11-25% (w/w) of the nanoparticles that comprise an outer surface comprising a cellular membrane and about 75-89% (w/w) of the nanoparticles that comprise an outer surface comprising a synthetic membrane, about 50% (w/w) of the nanoparticles that comprise an outer surface comprising a cellular membrane and about 50% (w/w) of the nanoparticles that comprise an outer surface comprising a synthetic membrane, about 51-75% (w/w) of the nanoparticles that comprise an outer surface comprising a cellular membrane and about 49-25% (w/w) of the nanoparticles that comprise an outer surface comprising a synthetic membrane, or about 90-100% (w/w) of the nanoparticles that comprise an outer surface comprising a cellular membrane and about 0-10% (w/w) of the nanoparticles that comprise an outer surface comprising a synthetic membrane.

In some embodiments, the nanoparticle used in the present methods substantially lacks immunogenicity to the subject, e.g., a mammal. For example, the cellular membrane can be derived from a source cell, e.g., e.g., a blood cell such as a red blood cell, a white blood cell, a platelet, or a macrophage, an endothelial cell, an epithelial cell, a neuronal cell, or a cardiac cell, derived from the same species of the mammal. In another example, the mammal is a human and the cellular membrane is derived from a human source cell, e.g., a human red blood cell. In some embodiments, the cellular membrane can be derived from a source cell, e.g., a red blood cell, of the mammal to be treated. For example, the cellular membrane can be derived from a human source cell, e.g., a human red blood cell, of the human to be treated.

The toxin can bind to the target cell and the source cell via any mechanism. In some embodiments, the toxin binds to the target cell and the source cell via the same mechanism. In other embodiments, the toxin binds to the target cell and the source cell via different mechanisms. In still other embodiments, the toxin can bind to the target cell via binding to a protein on the plasma membrane of the target cell. In yet other embodiments, the toxin can bind to the source cell via binding to a protein on the plasma membrane of the source cell.

The present methods can be used for decreasing or neutralizing the effect of a toxin that targets any target cell in a subject. In some embodiments, the present methods can be used for decreasing or neutralizing the effect of a toxin that targets a target cell derived primarily from endoderm, e.g., an exocrine secretory epithelial cell or a hormone secreting cell. In other embodiments, the present methods can be used for decreasing or neutralizing the effect of a toxin that targets a target cell derived primarily from ectoderm, e.g., a keratinizing epithelial cell, a wet stratified barrier epithelial cell, or a neuron. Exemplary neurons include a sensory transducer cell, an autonomic neuron cell, a sense organ and peripheral neuron supporting cell, a central nervous system neuron, a central nervous system glial cell and a lens cells. In still other embodiments, the present methods can be used for decreasing or neutralizing the effect of a toxin that targets a target cell derived primarily from mesoderm, e.g., a metabolism and storage cell, a barrier function cell, an extracellular matrix cell, a contractile cell, a blood and immune system cell, a germ cell, a nurse cell, or an interstitial cell. In some embodiments, the present methods can be used for decreasing or neutralizing the effect of a neuro-toxin.

The source cell and the target cell can be two different types of cells. Nanoparticles comprising a cellular membrane derived from any suitable source cell can be used in the present methods. In some embodiments, nanoparticles comprising a cellular membrane derived from a blood cell, an endothelial cell, an epithelial cell, a neuronal cell, or a cardiac cell can be used in the present methods. Exemplary blood cells include a red blood cell, a white blood cell, a platelet, and a macrophage. In some embodiments, a toxin targets a neuronal cell in a subject, and nanoparticles comprising a cellular membrane derived from a blood cell can be used for decreasing or neutralizing the effect of the toxin in the subject. For example, nanoparticles comprising a cellular membrane derived from a red blood cell, a white blood cell, a platelet, or a macrophage can be used for decreasing or neutralizing the effect of a toxin that targets a neuronal cell in a subject.

The present methods can be used for decreasing or neutralizing the effect of any suitable toxin that is an AchE inhibitor, e.g., a reversible AchE inhibitor or an irreversible AchE inhibitor, in a subject. Nanoparticles comprising a cellular membrane derived from any suitable source cell can be used in the present methods. In some embodiments, nanoparticles comprising a cellular membrane derived from a blood cell, an endothelial cell, an epithelial cell, a neuronal cell, and a cardiac cell can be used. In some embodiments, nanoparticles comprising a cellular membrane derived from a blood cell, e.g., a red blood cell, a white blood cell, a platelet, or a macrophage, can be used. In some embodiments, the toxin binds to an acetylcholinesterase (AchE) on the plasma membrane of the target cell, and nanoparticles comprising a cellular membrane derived from the plasma membrane of the source cell can be used.

Whether a toxin inhibits AchE can be assessed by any suitable methods. In some embodiments, whether a toxin inhibits AchE can be assessed by any suitable AchE activity assay. In one example, an AchE activity assay is based on Ellman's method using an alternative substrate acetylthiocholine and 5,5'-dithio-bis-2-nitrobenzoic acid (DTNB). The reaction results in production of 5-thio-2-nitrobenzoate that has yellow color due to the shift of electrons to the sulfur atom. See e.g., Ellman, G. L.; Courtney, D. K.; Andreas, V.; Featherstone, R. M. A new and rapid colorimetric determination of acetylcholinesterase activity. *Biochem. Pharmacol.* 1961, 7, 88-95; and Pohanka, M.; Jun, D.; Kuca, K. Inprovement of acetylcholinesterase-based assay for organophosphates in way of identification by reactivators. *Talanta* 2008, 77, 451-454. In another example, an AchE activity assay uses indoxylacetate as a substrate. See e.g., Pohanka et al., *Int. J. Mol. Sci.* 2011, 12, 2631-2640; doi:10.3390/ijms12042631. In still another example, an AchE activity assay uses acetylcholinesterase activity assay kit from Sigma-Aldrich, which is an optimized version of the Ellman method in which thiocholine, produced by AChE, reacts with 5,5'-dithiobis(2-nitrobenzoic acid) to form an colorimetric (412 nm) product, proportional to the AChE activity present. See e.g., Sigma-Aldrich Catalog Number MAK119.

The present methods can be used for decreasing or neutralizing the effect of any suitable toxin that is an organophosphate or an organophosphate poison in a subject. Organophosphate poisoning results from exposure to organophosphates (OPs), which cause the inhibition of acetylcholinesterase (AchE), leading to the accumulation of acetylcholine (Ach) in the body. In some embodiments, an organophosphate (sometimes abbreviated OP) or phosphate ester is the general name for esters of phosphoric acid. In other embodiments, "organophosphates" refer to a group of insecticides or nerve agents acting on the enzyme AchE. The term is used often to describe virtually any organic phosphorus (V)-containing compound, especially when dealing with neurotoxic compounds. Many of the so-called organophosphates contain C—P bonds. For instance, sarin is O-isopropyl methylphosphonofluoridate, which is formally derived from phosphorous acid $(HP(O)(OH)_2)$, not phosphoric acid $(P(O)(OH)_3)$. Also, many compounds which are derivatives of phosphinic acid are used as neurotoxic organophosphates. In still other embodiments, organophosphates have the following structural features: a terminal oxygen connected to phosphorus by a double bond, i.e., a phosphoryl group; two lipophilic groups bonded to the phosphorus; and a leaving group bonded to the phosphorus, often a halide. In yet other embodiments, an organophosphate has the following formula I:

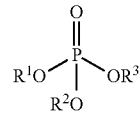

wherein each of $R^1$, $R^2$ and $R^3$ is independently an alkyl, an aryl, a lipophilic group, a hydrophilic group, and/or a leaving group. Exemplary organophosphates or organophosphate poisons include acephate (Orthene), aspon, Azinphos-Methyl (Guthion), Carbofuran (Furadan, F formulation), Carbophenothion (Trithion), Chlorfenvinphos (Birlane), Chlorpyrifos (Dursban, Lorsban), Coumaphos (Co-Ral), crotoxyphos (Ciodrin, Ciovap), crufomate (Ruelene), Demeton (Systox), Diazinon (Spectracide), dichlorvos (DDVP, Vapona), dicrotophos (Bidrin), Dimethoate (Cygon, De-Fend), dioxathion (Delnav), Disulfoton (Di-Syston), EPN, Ethion, Ethoprop (Mocap), famphur, fenamiphos (Nemacur), Fenitrothion (Sumithion)fensulfothion (Dasanit)fenthion (Baytex, Tiguvon), Fonofos (Dyfonate), isofenfos (Oftanol, Amaze), Malathion (Cython), Methamidophos (Monitor), methidathion (Supracide), methyl parathion, Mevinphos (Phosdrin), Monocrotophos, Naled (Dibrom), Nerve Agents (Sarin, soman, soman, VX), oxydemetonmethyl(Meta systox-R), Parathion (Niran, Phoskil), Phorate (Thimet), phosalone (Zolonc), phosmet (Imidan, Prolate), Phosphamidon (Dimecron), temephos (Abate), TEPP, Terbufos (Counter), tetrachlorvinphos (Rabon, Ravap) and Trichlorfon (Dylox, Neguvon). The present methods can be used for decreasing or neutralizing the effect of the above organophosphates or an organophosphate poisons in a subject.

The present methods can also be used for decreasing or neutralizing the effect of an organophosphate that is used as a nerve agent, a pesticide, an insecticide or a herbicide. Exemplary nerve agents include soman, sarin, tabun and VX. Exemplary insecticides include malathion, parathion, diazinon, fenthion, dichlorvos, chlorpyrifos, ethion, and trichlorfon (metrifonate). Exemplary herbicides include tribufos and merphos.

In some embodiments, the present methods can also be used for decreasing or neutralizing the effect of toxin that is an AchE inhibitor, e.g., an organophosphate, and at least partially effects its toxicity in the subject via inhibiting the AchE in or on the target cell, e.g., a neuronal cell and/or muscle cell. Exemplary neuronal cells include a motor and a sensory neuron. The target cell can be located at any suitable location in a subject. For example, the target cell can be a part of a neuromuscular junction, a cholinergic synapse, e.g., a cholinergic brain synapse, a central nervous tissue, a peripheral nervous tissue, a motor fiber, a sensory fiber, a motor and sensory fiber, a cholinergic fiber, or a noncholinergic fiber.

The present methods can be used for decreasing or neutralizing the effect of a toxin in a subject that is exposed to the toxin through any route or mechanism, such as inhalation, absorption, or ingestion. The present methods can also be used for decreasing or neutralizing the effect of a toxin in a subject that is exposed to the toxin as part of a warfare, a terror attack, a suicide attempt or an accident.

The present methods can further comprise administering another active ingredient to the subject. The other active ingredient can be used to decrease or neutralize the effect of the toxin in the subject. In some embodiments, the toxin is an organophosphate and the other active ingredient is an agent that protects AChE from inhibition by the organophosphate, an anti-cholinergic agent, an enzyme bioscavenger or a class III anti-arrhythmic agent. In one example, the agent that protects AChE from inhibition by the organophosphate is a carbamate. In another example, the anticholinergic agent is atropine, pralidoxime and/or a pyridinium oxime (e.g., trimedoxime or obidoxime). In still another example, the enzyme bioscavenger is a cholinesterase, e.g., human serum BChE (HuBChE).

In some embodiments, the present methods can further comprise administering a pharmaceutically acceptable carrier or excipient to the subject.

The composition used in the present methods can be administered using any suitable delivery mechanisms or techniques. In some embodiments, the composition can be administered alone. In other embodiments, the composition can be administered with a pharmaceutically acceptable carrier or excipient. In still other embodiments, the composition can be administered via a medicament delivery system or a medical device. Any suitable medicament delivery system or medical device can be used. For example, the medicament delivery system or the medical device can be an implant, e.g., an implant placed during or after bone surgery, a catheter, or a sustained-release drug delivery system.

In some embodiments, the present methods can further comprise assessing efficacy of the nanoparticle and/or the other active ingredient in decreasing or neutralizing the effect of a toxin in the subject. The efficacy of the nanoparticle and/or the other active ingredient in decreasing or neutralizing the effect of a toxin can be assessed by any suitable methods, e.g., in vitro and/or in vivo tests. In one example, the efficacy of the nanoparticle and/or the other active ingredient in decreasing or neutralizing the effect of a toxin can be assessed by assessing the binding between the toxin, e.g., an organophosphate, and a nanoparticle coated with a cellular membrane, e.g., a nanoparticle coated with a cellular membrane derived from a red blood cell. The binding between the toxin and the nanoparticle can be assessed by any suitable methods, e.g., by assessing the amount of the toxin bound to the nanoparticle, or by assessing the activity of a receptor or enzyme on the cellular membrane of the nanoparticle that binds to the toxin. In another example, the efficacy of the nanoparticle and/or the other active ingredient in decreasing or neutralizing the effect of a toxin can be assessed by assessing the removal of the toxin by the nanoparticle from a liquid. In still another example, the efficacy of the nanoparticle and/or the other active ingredient in decreasing or neutralizing the effect of a toxin can be assessed by assessing survival rate of an experimental animal when the experimental animal is exposed to a lethal dosage of the toxin and is treated with the nanoparticle and/or the other active ingredient. In yet another example, the efficacy of the nanoparticle and/or the other active ingredient in decreasing or neutralizing the effect of a toxin can be assessed by assessing or monitoring the activity of a receptor or enzyme that binds to the toxin in the treated subject, e.g., RBC AChE activity in the treated subject.

The composition used in the present methods can be administered to the subject via any suitable route of administration. In some embodiments, the nanoparticle used in the present methods, alone or in combination with other active ingredient(s), can be administered via oral, parenteral, rectal, nasal, topical, or ocular routes, or by inhalation. Exemplary parenteral administration can be via intravenous, intramuscular, intraperitoneal, intranasal, or subcutaneous route.

In another aspect, the present invention is directed to an use of an effective amount of a nanoparticle for the manufacture of a medicament for decreasing or neutralizing the effect of a toxin in a subject, wherein said nanoparticle comprises: a) an inner core comprising a non-cellular material, and b) an outer surface comprising a cellular membrane derived from a source cell, said toxin at least partially effects its toxicity in said subject via binding to a target cell of said subject, and 1) said source cell and said target cell are two different types of cells; or 2) said toxin is an acetylcholinesterase (AchE) inhibitor, and preferably, said source cell is selected from the group consisting of a blood cell, an endothelial cell, an epithelial cell, a neuronal cell, a cardiac cell and a muscle cell.

C. Combinations for Decreasing or Neutralizing the Effect of a Toxin in a Subject In still another aspect, the present invention is directed to a combination for decreasing or neutralizing the effect of a toxin in a subject, which combination comprises an effective amount of a nanoparticle and an effective amount of a second prophylactic or therapeutic agent for decreasing or neutralizing the effect of a toxin in a subject, wherein said nanoparticle comprises: a) an inner core comprising a non-cellular material, and b) an outer surface comprising a cellular membrane derived from a source cell, said toxin at least partially effects its toxicity in said subject via binding to a target cell of said subject, and 1) said source cell and said target cell are two different types of cells; or 2) said toxin is an acetylcholinesterase (AchE) inhibitor, and preferably, said source cell is selected from the group consisting of a blood cell, an endothelial cell, an epithelial cell, a neuronal cell, a cardiac cell and a muscle cell. In some embodiments, the toxin is not a toxin disclosed in U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011.

The present combination can be made, stored and/or used in any suitable formulation. In some embodiments, the present invention provides for a pharmaceutical composition comprising the above combination admixed with at least one pharmaceutically acceptable carrier or excipient. In other embodiments, the present invention provides for a method for decreasing or neutralizing the effect of a toxin in a subject, which method comprises administering, to a subject in need, or to cells of said subject, an effective amount of the above combination or pharmaceutical composition.

The above combination or pharmaceutical composition can be used to decrease or neutralize the effect of a toxin in a subject. In some embodiments, the subject is a mammal. In some embodiments, the mammal is a human. In other embodiments, the mammal is a non-human mammal, including a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

In some embodiments, the above combination or pharmaceutical composition can be used for decreasing the effect of a toxin in a subject. In other embodiments, the above combination or pharmaceutical composition can be used for neutralizing the effect of a toxin in a subject. The above combination or pharmaceutical composition can be used to decrease or neutralize the effect of a toxin in a subject to any suitable degree. For example, the above combination or pharmaceutical composition can be used to decrease or neutralize the effect of a toxin in a subject by at least 10%, 20%, 30%, 40%, 50%, 60%, 70%, 80%, 90%, 91%, 92%, 93%, 94%, 95%, 96%, 97%, 98%, 99% or more compared to a comparable untreated subject or to the same subject at an untreated stage.

The nanoparticle used in the above combination or pharmaceutical composition can comprise any suitable inner core. For example, the inner core of the nanoparticle can comprise a polymeric particle core, a silica particle core, or a metal, e.g., gold, particle core. Any suitable polymeric particle core can be used. In some embodiments, the polymeric particle core can comprise an optical shift property. In other embodiments, the polymeric particle core can comprise a metal, e.g., gold, iron oxide or a quantum dot. In still other embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In yet other embodiments, the inner core of the nanoparticle supports the outer surface.

The nanoparticle used in the above combination or pharmaceutical composition can comprise a cellular membrane derived from any suitable source cell. For example, the nanoparticle can comprise a plasma membrane or an intracellular membrane derived from any suitable source cell. In some embodiments, the nanoparticle can comprise an intracellular membrane derived from any suitable source cell e.g., a blood cell such as a red blood cell, a white blood cell, a platelet, or a macrophage, an endothelial cell, an epithelial cell, a neuronal cell, or a cardiac cell. In other embodiments, the nanoparticle can comprise a plasma membrane derived from any suitable source cell, e.g., a blood cell such as a red blood cell, a white blood cell, a platelet, or a macrophage, an endothelial cell, an epithelial cell, a neuronal cell, or a cardiac cell.

The therapeutic agent, the prophylactic agent, the diagnostic or marker agent, the prognostic agent, the isolation agent, the monitoring agent, or a combination thereof, can be comprised in any suitable location in the above combination or pharmaceutical composition. For example, the therapeutic agent, the prophylactic agent, the diagnostic or marker agent, the prognostic agent, the isolation agent, the monitoring agent, or a combination thereof, can be comprised in the nanoparticle. In some embodiments, the therapeutic agent, the prophylactic agent, the diagnostic or marker agent, the prognostic agent, the isolation agent, the monitoring agent, or a combination thereof, can be comprised in a releasable cargo in the nanoparticle. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or cells of the subject, or by a change of a physical parameter surrounding the nanoparticle. The nanoparticle can comprise any suitable type of a releasable cargo. For example, the releasable cargo can be a metallic particle, a polymeric particle, a dendrimer particle, or an inorganic particle. In some embodiments, the therapeutic agent, the prophylactic agent, the diagnostic or marker agent, the prognostic agent, the isolation agent, the monitoring agent, or a combination thereof, can be comprised in the composition used in the above combination or pharmaceutical composition but outside the nanoparticle.

The nanoparticle used in the above combination or pharmaceutical composition can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm, or any sub-range within about 10 nm to about 10 μm, e.g., any range between any two of the above sizes.

The nanoparticle used in the above combination or pharmaceutical composition can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle in the above combination or pharmaceutical composition substantially lacks constituents of the source cell, e.g., a blood cell such as a red blood cell, a white blood cell, a platelet, or a macrophage, an endothelial cell, an epithelial cell, a neuronal cell, or a cardiac cell, from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the source cell, e.g., a blood cell such as a red blood cell, a white blood cell, a platelet, or a macrophage, an endothelial cell, an epithelial cell, a neuronal cell, or a cardiac cell, from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle in the above combination or pharmaceutical composition substantially maintains natural structural integrity or activity of the cellular membrane derived from a source cell or the constituents of the cellular membrane derived from a source cell so that the nanoparticle functions as decoy for the toxin's target cell, e.g., neuronal cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for functioning as decoy for the toxin's target cell, e.g., neuronal cells.

In some embodiments, the nanoparticle in the above combination or pharmaceutical composition is biocompatible or biodegradable. For example, the inner core of the nanoparticle comprises PLGA and the outer surface of the nanoparticle comprises a plasma membrane derived from a source cell, e.g., a blood cell such as a red blood cell, a white blood cell, a platelet, or a macrophage, an endothelial cell, an epithelial cell, a neuronal cell, or a cardiac cell.

The nanoparticle in the above combination or pharmaceutical composition can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours, e.g., about 1, 2, 3, 4, 5, 6, 7, 8, 9, 10, 15, 20, 25, 30, 35 or 40 hours.

The outer surface of the nanoparticle used in above combination or pharmaceutical composition can further comprise a synthetic membrane. In some embodiments, the nanoparticles used in the above combination or pharmaceutical composition comprise a mixture of nanoparticles that comprise an outer surface comprising a cellular membrane and nanoparticles that comprise an outer surface comprising a synthetic membrane. The nanoparticles that comprise an outer surface comprising a synthetic membrane may or may not absorb or bind to a toxin. In some embodiments, both the nanoparticles that comprise an outer surface comprising a cellular membrane and nanoparticles that comprise an outer surface comprising a synthetic membrane absorb or bind to a toxin. In other embodiments, the nanoparticles that comprise an outer surface comprising a cellular membrane absorb or bind to a toxin, but the nanoparticles that comprise an outer surface comprising a synthetic membrane do not absorb or bind to a toxin.

The above combination or pharmaceutical composition can comprise the nanoparticles that comprise an outer surface comprising a cellular membrane and nanoparticles that comprise an outer surface comprising a synthetic membrane in any suitable ratio. In some embodiments, the above combination or pharmaceutical composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a cellular membrane. In other embodiments, the above combination or pharmaceutical composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a synthetic membrane. For example, the above combination or pharmaceutical composition can comprise about 1-10% (w/w) of the nanoparticles that comprise an outer surface comprising a cellular membrane and about 90-99% (w/w) of the nanoparticles that comprise an outer surface comprising a synthetic membrane, about 11-25% (w/w) of the nanoparticles that comprise an outer surface comprising a cellular membrane and about 75-89% (w/w) of the nanoparticles that comprise an outer surface comprising a synthetic membrane, about 50% (w/w) of the nanoparticles that comprise an outer surface comprising a cellular membrane and about 50% (w/w) of the nanoparticles that comprise an outer surface comprising a synthetic membrane, about 51-75% (w/w) of the nanoparticles that comprise an outer surface comprising a cellular membrane and about 49-25% (w/w) of the nanoparticles that comprise an outer surface comprising a synthetic membrane, or about 90-100% (w/w) of the nanoparticles that comprise an outer surface comprising a cellular membrane and about 0-10% (w/w) of the nanoparticles that comprise an outer surface comprising a synthetic membrane.

In some embodiments, the nanoparticle used in the above combination or pharmaceutical composition substantially lacks immunogenicity to the subject, e.g., a mammal. For example, the cellular membrane can be derived from a source cell, e.g., e.g., a blood cell such as a red blood cell, a white blood cell, a platelet, or a macrophage, an endothelial cell, an epithelial cell, a neuronal cell, or a cardiac cell, derived from the same species of the mammal. In another example, the mammal is a human and the cellular membrane is derived from a human source cell, e.g., a human red blood cell. In some embodiments, the cellular membrane can be derived from a source cell, e.g., a red blood cell, of the mammal to be treated. For example, the cellular membrane can be derived from a human source cell, e.g., a human red blood cell, of the human to be treated.

The toxin can bind to the target cell and the source cell via any mechanism. In some embodiments, the toxin binds to the target cell and the source cell via the same mechanism. In other embodiments, the toxin binds to the target cell and the source cell via different mechanisms. In still other embodiments, the toxin can bind to the target cell via binding to a protein on the plasma membrane of the target cell. In yet other embodiments, the toxin can bind to the source cell via binding to a protein on the plasma membrane of the source cell.

The above combination or pharmaceutical composition can be used for decreasing or neutralizing the effect of a toxin that targets any target cell in a subject. In some embodiments, the above combination or pharmaceutical composition can be used for decreasing or neutralizing the effect of a toxin that targets a target cell derived primarily from endoderm, e.g., an exocrine secretory epithelial cell or a hormone secreting cell. In other embodiments, the above combination or pharmaceutical composition can be used for decreasing or neutralizing the effect of a toxin that targets a target cell derived primarily from ectoderm, e.g., a keratinizing epithelial cell, a wet stratified barrier epithelial cell, or a neuron. Exemplary neurons include a sensory transducer cell, an autonomic neuron cell, a sense organ and peripheral neuron supporting cell, a central nervous system neuron, a central nervous system glial cell and a lens cells. In still other embodiments, the above combination or pharmaceutical composition can be used for decreasing or neutralizing the effect of a toxin that targets a target cell derived primarily from mesoderm, e.g., a metabolism and storage cell, a barrier function cell, an extracellular matrix cell, a contractile cell, a blood and immune system cell, a germ cell, a nurse cell, or an interstitial cell. In some embodiments, the above combination or pharmaceutical composition can be used for decreasing or neutralizing the effect of a neuro-toxin.

The source cell and the target cell can be two different types of cells. Nanoparticles comprising a cellular membrane derived from any suitable source cell can be used in the above combination or pharmaceutical composition. In some embodiments, nanoparticles comprising a cellular membrane derived from a blood cell, an endothelial cell, an epithelial cell, a neuronal cell, or a cardiac cell can be used in the above combination or pharmaceutical composition. Exemplary blood cells include a red blood cell, a white blood cell, a platelet, and a macrophage. In some embodiments, a toxin targets a neuronal cell in a subject, and nanoparticles comprising a cellular membrane derived from a blood cell can be used for decreasing or neutralizing the effect of the toxin in the subject. For example, nanoparticles comprising a cellular membrane derived from a red blood cell, a white blood cell, a platelet, or a macrophage can be used for decreasing or neutralizing the effect of a toxin that targets a neuronal cell in a subject.

The above combination or pharmaceutical composition can be used for decreasing or neutralizing the effect of any suitable toxin that is an AchE inhibitor, e.g., a reversible AchE inhibitor or an irreversible AchE inhibitor, in a subject. Nanoparticles comprising a cellular membrane derived from any suitable source cell can be used in the above combination or pharmaceutical composition. In some embodiments, nanoparticles comprising a cellular membrane derived from a blood cell, an endothelial cell, an epithelial cell, a neuronal cell, and a cardiac cell can be used. In some embodiments, nanoparticles comprising a cellular membrane derived from a blood cell, e.g., a red blood cell, a white blood cell, a platelet, or a macrophage, can be used. In some embodiments, the toxin binds to an acetylcholinesterase (AchE) on the plasma membrane of the target cell, and nanoparticles comprising a cellular membrane derived from the plasma membrane of the source cell can be used.

Whether a toxin inhibits AchE can be assessed by any suitable methods. In some embodiments, whether a toxin inhibits AchE can be assessed by any suitable AchE activity assay. In one example, an AchE activity assay is based on Ellman's method using an alternative substrate acetylthiocholine and 5,5'-dithio-bis-2-nitrobenzoic acid (DTNB). The reaction results in production of 5-thio-2-nitrobenzoate that has yellow color due to the shift of electrons to the sulfur atom. See e.g., Ellman, G. L.; Courtney, D. K.; Andreas, V.; Featherstone, R. M. A new and rapid colorimetric determination of acetylcholinesterase activity. *Biochem. Pharmacol.* 1961, 7, 88-95; and Pohanka, M.; Jun, D.; Kuca, K. Inprovement of acetylcholinesterase-based assay for organophosphates in way of identification by reactivators. *Talanta* 2008, 77, 451-454. In another example, an AchE activity assay uses indoxylacetate as a substrate. See e.g., Pohanka et al., *Int. J. Mol. Sci.* 2011, 12, 2631-2640; doi:10.3390/ijms12042631. In still another example, an AchE activity assay uses acetylcholinesterase activity assay kit from Sigma-Aldrich, which is an optimized version of the Ellman method in which thiocholine, produced by AChE, reacts with 5,5'-dithiobis(2-nitrobenzoic acid) to form an colorimetric (412 nm) product, proportional to the AChE activity present. See e.g., Sigma-Aldrich Catalog Number MAK119.

The above combination or pharmaceutical composition can be used for decreasing or neutralizing the effect of any suitable toxin that is an organophosphate or an organophosphate poison in a subject. Organophosphate poisoning results from exposure to organophosphates (OPs), which cause the inhibition of acetylcholinesterase (AchE), leading to the accumulation of acetylcholine (Ach) in the body. In some embodiments, an organophosphate (sometimes abbreviated OP) or phosphate ester is the general name for esters of phosphoric acid. In other embodiments, "organophosphates" refer to a group of insecticides or nerve agents acting on the enzyme AchE. The term is used often to describe virtually any organic phosphorus(V)-containing compound, especially when dealing with neurotoxic compounds. Many of the so-called organophosphates contain C—P bonds. For instance, sarin is O-isopropyl methylphosphonofluoridate, which is formally derived from phosphorous acid (HP(O)(OH)$_2$), not phosphoric acid (P(O)(OH)$_3$). Also, many compounds which are derivatives of phosphinic acid are used as neurotoxic organophosphates. In still other embodiments, organophosphates have the following structural features: a terminal oxygen connected to phosphorus by a double bond, i.e., a phosphoryl group; two lipophilic groups bonded to the phosphorus; and a leaving group bonded to the phosphorus, often a halide. In yet other embodiments, an organophosphate has the following formula I:

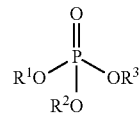

wherein each of R$^1$, R$^2$ and R$^3$ is independently an alkyl, an aryl, a lipophilic group, a hydrophilic group, and/or a leaving group. Exemplary organophosphates or organophosphate poisons include acephate (Orthene), aspon, Azinphos-Methyl (Guthion), Carbofuran (Furadan, F formulation), Carbophenothion (Trithion), Chlorfenvinphos (Birlane), Chlorpyrifos (Dursban, Lorsban), Coumaphos (Co-Ral), crotoxyphos (Ciodrin, Ciovap), crufomate (Ruelene), Demeton (Systox), Diazinon (Spectracide), dichlorvos (DDVP, Vapona), dicrotophos (Bidrin), Dimethoate (Cygon, De-Fend), dioxathion (Delnav), Disulfoton (Di-Syston), EPN, Ethion, Ethoprop (Mocap), famphur, fenamiphos (Nemacur), Fenitrothion (Sumithion)fensulfothion (Dasanit)fenthion (Baytex, Tiguvon), Fonofos (Dyfonate), isofenfos (Oftanol, Amaze), Malathion (Cython), Methamidophos (Monitor), methidathion (Supracide), methyl parathion, Mevinphos (Phosdrin), Monocrotophos, Naled (Dibrom), Nerve Agents (Sarin, soman, soman, VX), oxydemetonmethyl(Meta systox-R), Parathion (Niran, Phoskil), Phorate (Thimet), phosalone (Zolonc), phosmet (Imidan, Prolate), Phosphamidon (Dimecron), temephos (Abate), TEPP, Terbufos (Counter), tetrachlorvinphos (Rabon, Ravap) and Trichlorfon (Dylox, Neguvon). The above combination or pharmaceutical composition can be used for decreasing or neutralizing the effect of the above organophosphates or an organophosphate poisons in a subject.

The above combination or pharmaceutical composition can also be used for decreasing or neutralizing the effect of an organophosphate that is used as a nerve agent, a pesticide, an insecticide or a herbicide. Exemplary nerve agents include soman, sarin, tabun and VX. Exemplary insecticides include malathion, parathion, diazinon, fenthion, dichlorvos, chlorpyrifos, ethion, and trichlorfon (metrifonate). Exemplary herbicides include tribufos and merphos.

In some embodiments, the above combination or pharmaceutical composition can also be used for decreasing or neutralizing the effect of toxin that is an AchE inhibitor, e.g., an organophosphate, and at least partially effects its toxicity in the subject via inhibiting the AchE in or on the target cell, e.g., a neuronal cell and/or muscle cell. Exemplary neuronal cells include a motor and a sensory neuron. The target cell can be located at any suitable location in a subject. For example, the target cell can be a part of a neuromuscular junction, a cholinergic synapse, e.g., a cholinergic brain synapse, a central nervous tissue, a peripheral nervous tissue, a motor fiber, a sensory fiber, a motor and sensory fiber, a cholinergic fiber, or a noncholinergic fiber.

The above combination or pharmaceutical composition can be used for decreasing or neutralizing the effect of a toxin in a subject that is exposed to the toxin through any route or mechanism, such as inhalation, absorption, or ingestion. The above combination or pharmaceutical composition can also be used for decreasing or neutralizing the effect of a toxin in a subject that is exposed to the toxin as part of a warfare, a terror attack, a suicide attempt or an accident.

The above combination or pharmaceutical composition can comprise any suitable active ingredient that can be used to decrease or neutralize the effect of the toxin in the subject. In some embodiments, the toxin is an organophosphate and the other active ingredient is an agent that protects AChE from inhibition by the organophosphate, an anti-cholinergic agent, an enzyme bioscavenger or a class III anti-arrhythmic agent. In one example, the agent that protects AChE from inhibition by the organophosphate is a carbamate. In another example, the anti-cholinergic agent is atropine, pralidoxime and/or a pyridinium oxime (e.g., trimedoxime or obidoxime). In still another example, the enzyme bioscavenger is a cholinesterase, e.g., human serum BChE (HuBChE).

The above combination or pharmaceutical composition can be administered using any suitable delivery mechanisms or techniques. In some embodiments, the above combination or pharmaceutical composition can be administered alone. In other embodiments, the above combination or pharmaceutical composition can be administered with a pharmaceutically acceptable carrier or excipient. In still other embodiments, the above combination or pharmaceutical composition can be administered via a medicament delivery system or a medical device. Any suitable medicament delivery system or medical device can be used. For example, the medicament delivery system or the medical device can be an implant, e.g., an implant placed during or after bone surgery, a catheter, or a sustained-release drug delivery system.

The above combination or pharmaceutical composition can be administered to the subject via any suitable route of administration. In some embodiments, the above combination or pharmaceutical composition can be administered via oral, parenteral, rectal, nasal, topical, or ocular routes, or by inhalation. Exemplary parenteral administration can be via intravenous, intramuscular, intraperitoneal, intranasal, or subcutaneous route.

D. Pharmaceutical Compositions and Administration Routes

The pharmaceutical compositions comprising the nanoparticles, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanoparticles, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the nanoparticles, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The nanoparticles, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the nanoparticles, alone or in combination with another active ingredient, may be provided in a solid form, such as a tablet or capsule, or as a solution, emulsion, or suspension. To prepare the oral compositions, the nanoparticles, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanoparticles, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the nanoparticles, alone or in combination with other active ingredient(s), may be administered using, for example, a spray formulation also containing a suitable carrier.

For topical applications, the nanoparticles, alone or in combination with other active ingredient(s), are preferably formulated as creams or ointments or a similar vehicle suitable for topical administration. For topical administration, the nanoparticles, alone or in combination with other active ingredient(s), may be mixed with a pharmaceutical carrier at a concentration of about 0.1% to about 10% of drug to vehicle. Another mode of administering the nanoparticles, alone or in combination with other active ingredient(s), may utilize a patch formulation to effect transdermal delivery.

In certain embodiments, the present disclosure provides pharmaceutical composition comprising the nanoparticles, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

E. Example 1. Detoxification of Organophosphate Poisoning Using Nanoparticle Bioscavengers The activities of serum cholinesterases in the blood, which include both AChE and BChE, are the most widely used markers for diagnosing OP poisoning (14). Whereas BChE exist primarily as freely soluble forms in the plasma, AChE is a membrane-anchored protein observed commonly on red blood cell (RBC) membranes, neuromuscular junctions and cholinergic brain synapses. Recent advances in nanotechnology, particularly in cell membrane cloaked nanoparticles, have provided an opportunity for the membrane-bound AChE to be exploited for biomedical applications. It has been demonstrated that the cell membrane cloaking approach enables membrane proteins to be controllably anchored and displayed in a right-side-out manner on nanoscale particulates (15-17), and the resulting biomimetic nanoparticles have been used for various biomedical functions, including bioscavenger application for absorbing protein toxins and auto-reactive immune factors (15, 18). It is conceivable that the platform may permit the systemic administration of cell membrane-associated AChE to intercept toxic OPs in the bloodstream. To demonstrate OP detoxification using the biomimetic nanoparticles, herein we prepared RBC membrane-cloaked nanoparticles (denoted "RBC-NPs") to exploit the RBC's surface AChE for OP scavenging (FIG. 1). Dichlorvos (DDVP), one of the most widely used compounds in organophosphorus pesticides, is used as a model OP in this study. We showed that following cell membrane cloaking, the RBC-NPs retain the membrane-bound AChE as well as their enzymatic activity. The biomimetic nanoparticle were applied as an OP scavenger to help maintain endogenous cholinesterase activity following OP exposure.

Results

Figure 2A:
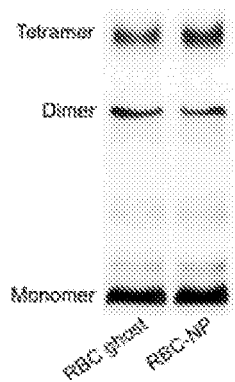
FIGS. 2A-2F. In vitro characterization of RBC-NPs and RBC-NP/DDVP complex. (2A) Western blotting showing RBC ghosts and RBC-NPs have similar blotting patterns following anti-AChE staining. (2B) Quantification of western blot band intensity showing RBC ghosts and RBC-NPs contain equivalent amounts of AChE, indicating little loss of membrane-bound AchE during the RBC-NP preparation. (2C) AChE activity test showing RBC-NP and RBC ghosts prepared from equivalent membrane content have similar AChE activity. (2D) TEM image demonstrates the core/shell structure of RBC-NP/DDVP complex. Scale bar=100 nm. (2E) Size and (2F) surface zeta potential of RBC-NP and RBC-NP/DDVP complex. All error bars represent standard error of mean.
Figure 2B:
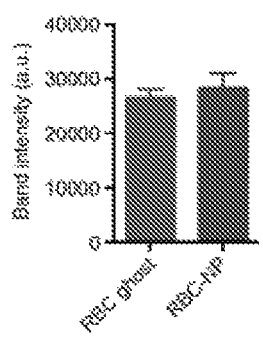
Figure 2C:
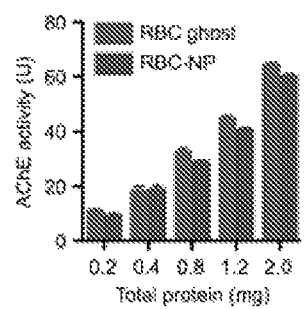
Figure 2D:
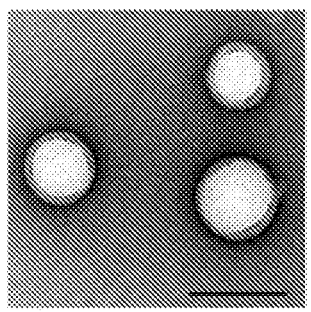
Figure 2E:
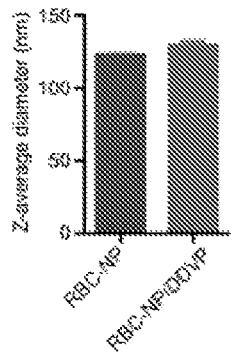
Figure 2F:
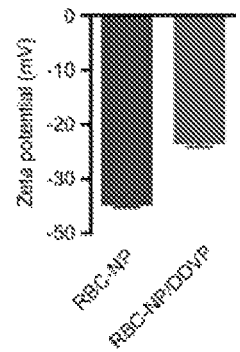
Figure 4A:
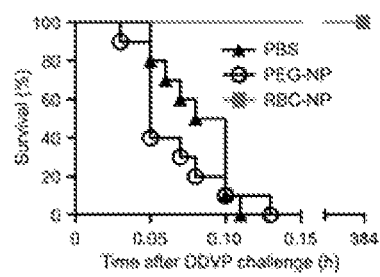
FIGS. 4A-4D. In vivo neutralization of DDVP by RBC-NPs. (4A) Survival curve of mice over 16 days and (4B) relative RBC AChE activity of mice following intravenous administration of 200 mg/kg of RBC-NPs or PEG-NPs immediately after an intravenous injection of DDVP at a lethal dose (10 mg/kg) (n=10). (4C) Survival curve of mice over 16 days and (4D) relative RBC AChE activity of mice following administration of 200 mg/kg of RBC-NPs or PEG-NPs immediately after oral administration of DDVP at a lethal dose (150 mg/kg) (n=10). All error bars represent standard error of mean.
Figure 4B:
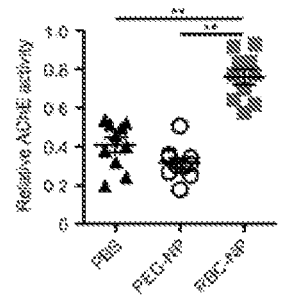
Figure 4C:
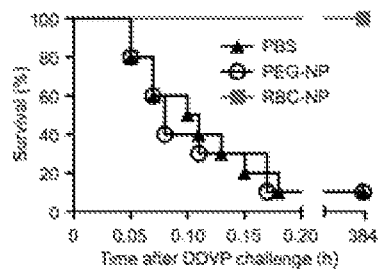
Figure 4D:
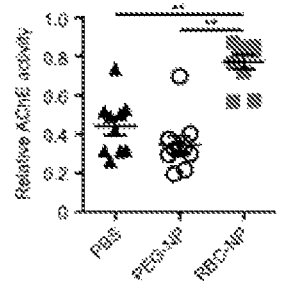
Figure 5A:
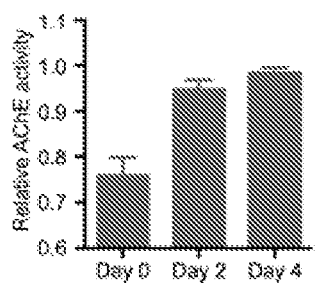
FIGS. 5A-5D. RBC AChE activity recovery following OP detoxification by RBC-NPs. (5A) Relative RBC AChE activity recovered over a span of 4 days after the mice were challenged intravenously with DDVP (10 mg/kg) and immediately treated with RBC-NPs (200 mg/kg) (n=10). (5B) Relative RBC AChE activity recovered over a span of 4 days after mice were challenged orally with DDVP (150 mg/kg) and immediately treated with RBC-NPs (200 mg/kg) (n=10). (5C) Biodistribution of RBC-NP/DDVP complex 24 h after intravenous injection. (5D) Hematoxylin and eosin (H&E) stained liver histology showed no tissue damage on day 3 (top) and day 7 (bottom) following RBC-NP/DDVP complex injections. Each image is representative of five examined sections. Scale bar=150 μm. All error bars represent standard error of mean.
Figure 5B:
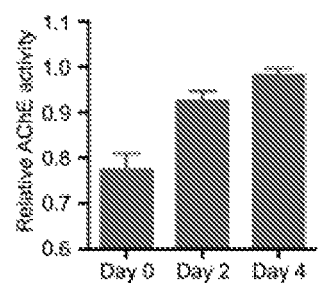
Figure 5C:
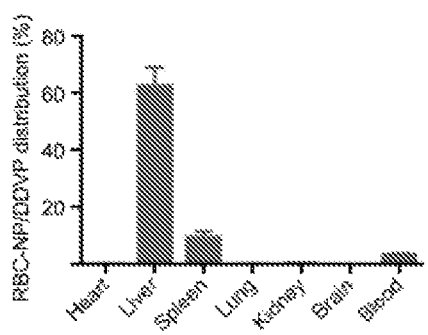
Figure 5D:
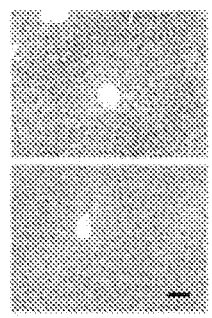

RBC-NPs were prepared according to a previously reported protocol in which purified RBC membranes were coated onto 100 nm poly(lactic-co-glycolic acid) (PLGA) polymeric cores via a sonication approach. To investigate the retention of AChE in the resulting RBC-NPs, western blotting was conducted on RBC ghosts and RBC-NPs of equivalent membrane content. It was shown that following staining with anti-AChE antibodies, RBC-NPs had similar banding patterns to RBC ghosts, including bands that correspond to monomers, dimers, and tetramers of the protein (FIG. 2A). Total blotting intensity analyzed by ImageJ demonstrated that there was no statistically significant difference in the total blotting intensity between RBC ghosts and RBC-NPs, indicating efficient translocation of membrane proteins onto the nanoparticle substrates (FIG. 2B). Further examination of AChE activity showed that RBC-NPs and RBC ghosts had largely similar AChE activity (FIG. 2C). These results indicate that after nanoparticle preparation, there was minimal loss of membrane-associated AChE content and little alteration in AChE enzyme activity, which is consistent with previous findings that demonstrated preservation of surface protein functionality on these cell membrane-cloaked nanoparticles (16, 19). Given the well studied reactivity between OPs and AChE, we then examined the effect of DDVP on the physicochemical properties of the RBC-NPs. Transmission electron microscopy (TEM) revealed that following mixing with DDVP, the RBC-NPs retained a core/shell structure that corresponds to unilamellar membrane coatings over the nanoparticle (FIG. 2D). In addition, dynamic light scattering measurements showed that RBC-NPs remained similar in size following DDVP exposure (FIG. 2E), indicating that the DDVP reaction had little effect on the RBC-NPs' structure and stability. An increase in the particles' zeta potential was observed following incubation with DDVP (FIG. 2F), which can likely be attributed to the surface charge shielding effect by the bound DDVP molecules.

To investigate the ability of RBC-NPs to scavenge OPs, 0.4 and 0.1 mg of the particles suspended in 100 μL of aqueous solution was incubated with different concentrations of DDVP ranging from approximately 1 μg/mL to 1 mg/mL for 30 min Following nanoparticle removal via centrifugation, the amount of nanoparticle-associated DDVP was quantified by measuring the remaining DDVP concentration in the supernatant via high performance liquid chromatography (HPLC). It can be observed that RBC-NP/DDVP association occurs in a concentration-dependent manner (FIG. 3A). A 4-fold increase in RBC-NP concentration correlated well with the observed right shift in absorption capacity, reflecting the 1:1 stoichiometry behind the covalent interaction between OPs and AChE. We also titrated RBC-NPs in a reaction mixture with 100 μL of aqueous solution and 5 μg of DDVP (FIG. 3B). It was observed that to absorb 50% or 2.5 μg of DDVP, approximately 32 μg of RBC-NP was needed. A saturation level was reached as the RBC-NP concentration was raised above 1 mg/mL. To evaluate the specificity of DDVP removal by RBC-NPs, different nanoformulations, including 0.4 mg of RBC-NPs, PEGylated NPs (PEG-NPs) and PEG-liposomes were incubated with 5 μg of DDVP for 30 min (FIG. 3C). Almost all DDVP was removed by the RBC-NPs whereas PEG-NPs and PEG-liposomes showed little DDVP removal, indicating that only RBC-NPs have the capacity to remove DDVP. Furthermore, in vitro AChE protection efficacy was evaluated by co-incubating RBC ghosts with increasing concentrations of DDVP in the presence of RBC-NPs (FIG. 3D). Following 30 min of incubation, the RBC ghosts were isolated from the reaction mixtures and examined for AChE activity. It was observed that the DDVP concentrations required to inhibit 50% of the AChE activity on the RBC ghosts were 10, 43, and 312 μg/mL for the mixtures containing 0, 1, and 4 mg/mL of RBC-NPs, respectively. The increased retention of AChE activity on RBC ghosts validated the scavenging effect of RBC-NPs. Comparison of different nanocarriers' anti-OP effect was performed using 4 mg/mL of PEG-NPs, PEG-liposomes, and RBC-NPs incubated with 5 μg of DDVP and 2% of RBC ghosts in 100 μL of reaction mixtures (FIG. 3E). Following 30 min of incubation, isolated RBC ghosts were analyzed for their AChE activity. The RBC-NP group showed significantly higher AChE activity retention on the RBC ghosts as compared to the other nanoformulations. Approximately 90% of RBC ghosts' AChE activity was preserved in the presence of RBC-NPs, corroborating the receptor-specific anti-OP effect enabled by the biomimetic nanoparticles.

To examine the potential of RBC-NPs to detoxify DDVP in vivo, we used a mouse model of OP poisoning with either intravenous or oral administrations of DDVP. For intravenous DDVP administration, a lethal dose of DDVP (10 mg/kg) capable of inducing acute death in mice was injected via the tail vein. Mice in the treatment group received an intravenous injection of RBC-NPs or PEG-NPs at a dose of 200 mg/kg. It was shown that the mice without any treatment had a 100% mortality rate within 7 min after DDVP injection (FIG. 4A). In the group treated with RBC-NPs, all mice survived the lethal DDVP challenge (n=10, $p<0.0001$). In contrast, PEG-NPs failed to improve the survival rate of the DDVP-challenged mice and there was no significance in survival between the PEG-NP-treated group and the non-treatment group ($p=0.380$). Assaying the circulatory RBC AChE activity following the DDVP challenge and treatments further demonstrated that RBC-NPs significantly increased RBC AChE activity as compared to the PEG-NP group ($p<0.001$) and the non-treatment group ($p<0.001$) (FIG. 4B), whereas no statistical significance was observed in the circulatory RBC AChE activity between the PEG-NP-treated group and the non-treatment group ($p=0.226$). For oral DDVP challenge, mice were orally administered with a lethal dose of DDVP (150 mg/kg). Mice in the treatment group received an intravenous injection of RBC-NP or PEG-NP at a dose 200 mg/kg. It was shown that 90% of mice without any treatment died within 11 min after DDVP administration (FIG. 4C). RBC-NP treatment remained beneficial to the overall survival with a 100% survival rate ($p=0.0002$, n=10), whereas PEG-NP treatment showed no survival advantage ($p=0.8989$). The RBC AChE levels for the orally DDVP challenged mice were consistent with the intravenously challenged ones. Whereas RBC-NP treatment resulted in significant RBC AChE activity retention in circulation as compared to the non-treatment group ($p<0.001$), no statistical significance in AChE activity was observed between the non-treatment group and the PEG-NP treatment group ($p=0.362$) (FIG. 4D).

Recovery following DDVP poisoning was also investigated using circulatory RBC AChE activity as a marker (FIGS. 5A and 5B). It was shown that, by day 4, the RBC AChE activity returned to normal levels in those mice treated with RBC-NPs. This indicates the eventual clearance of OPs and the replenishment of cholinesterase content in circulation. To examine the in vivo fate of DDVP detoxified by RBC-NPs, the biodistribution of the RBC-NPs loaded with DDVP was studied. It was shown that RBC-NP/DDVP complex accumulated primarily in the liver (FIG. 5C). Hematoxylin and eosin (H&E) stained liver histology on days 3 and 7 following the administration of RBC-NP/DDVP revealed normal hepatocytes supplied by blood vessels with no inclusion of Kupffer cells in the sinusoids (FIG. 5D). The lack of liver tissue damage suggests that the sequestered DDVP was safely metabolized, showing minimal residual toxicity upon tissue distribution.

Discussion

OP poisoning remains a major public health issue as it is associated with high morbidity and mortality rates. Highly toxic OPs are considered one of the most dangerous chemical warfare agents and greatly threaten the safety of both military and civilian populations. OPs induce their acute toxicological effects through inhibition of AChE, which leads to an accumulation of ACh at synapses followed by overstimulation of cholinergic receptors and the disruption of neurotransmission. Deaths can occur within a few minutes after serious OP poisoning, which are generally due to respiratory failures mediated by several mechanisms. Paralysis of respiratory muscles resulting from failure of nicotinic ACh receptors is a primary cause of OP-induced lethality, and overstimulation of peripheral muscarinic receptors can also lead to choking due to excessive bronchorrhea and bronchoconstriction. Brain damage is another severe effect of OP intoxication as hydrophobic OPs readily cross the blood-brain barrier to exert their effects on the central nervous system. Therefore, anti-OP therapy needs to prevent OPs' pathophysiological effects in a direct and effective manner.

Currently, treatment of OP poisoning remains challenging (20). Very few therapeutic options have been developed since the 1950's and 1970's, when anticholinergic drugs, carbamate-based pretreatment, pyridinium oximes, and benzodiazepines were introduced as anti-OP countermeasures in emergency situations (21). Research on medical intervention against OP poisoning has been relatively static, with atropine, a standard antidote in the 1940's, remaining the primary anti-OP treatment. It is the only universally accepted treatment for muscarinic symptoms such as miosis, bronchospasm, vomiting, increased sweating, diarrhea, and urinary incontinence. However, despite its acceptance, there is no universal guideline on its administration and dosing. Under-dosing can delay optimal atropinization, resulting in death from central respiratory depression, hypoxia, and hypotension. Conversely, overdosing may lead to excessive anticholinergic toxicity, which can be fatal in severe cases (22). Oximes are a unique class of anti-OP countermeasures, as they remove nerve agents from inhibited AChE to reactivate its activity. However, the efficacy of oxime therapy is still in debate. AChE inhibition by several nerve agents (e.g. tabun and soman) has been shown to be irreversible despite the application of clinically used oxime, as cholinesterases undergo rapid conversion into a non-reactivatable form upon phosphorylation (23). Despite extensive research and development, there is not a single, broad-spectrum oxime suitable for antidotal treatment against all OP agents (24).

Bioscavenger therapy has more recently emerged as a medical countermeasure to detoxify OPs in the bloodstream. These scavengers can be either stoichiometric (mole-to-mole neutralization) or catalytic (facilitating OP hydrolysis). PON-1, for instance, is the leading catalytic bioscavenger under development (10, 12). PON-1 is a calcium-dependent enzyme that hydrolyzes numerous OPs at a high efficiency (25). Intravenous administration of purified PON-1 has been shown to protect guinea pigs against sarin and soman (26, 27). However, there are limitations regarding large-scale production and use of PON-1 as a therapeutic candidate. These include difficulties in producing recombinant PON-1 using microbial expression systems, low hydrolytic activity of wild-type PON-1 towards certain substrates, and low storage stability of the purified enzyme. HuBChE is another leading bioscavenger candidate. It is estimated that 200 mg of these stoichiometric anti-OP scavengers can protect a human against two times the $LD_{50}$ dose of soman (28). Animal studies in guinea pigs revealed that administration of large doses of HuBChE confer protection against up to 5.5 times the $LD_{50}$ of soman or 8 times the $LD_{50}$ of VX (29). However, the lack of an affordable source of the enzyme remains a major hurdle in its translation. HuBChE isolation from human blood is economically prohibitive, and alternative production strategies using transgenic organisms pose immunogenicity concerns. Among other anti-OP candidates, AChE represents a promising bioscavenger with higher stereoselectivity than BuChE. Human AChE has been shown to more efficiently scavenge VX agents as compared to human HuBChE (30, 31). Unfortunately, development of AChE as a stoichiometric bioscavenger has been discontinued due to similar translational challenges (21). Given this landscape, alternative strategies in developing OP bioscavengers can be of great therapeutic impact.

Nanoparticles have been developed rapidly over the past years due to their great potential in drug delivery. More recently, nanoparticles have been applied to remove toxins or chemicals from blood for biodetoxification (32, 33). To this end, little work has been done to apply nanoparticles as antidotes against OP poisoning. Here, we demonstrated that nanoparticles engineered with a biomimetic surface could be applied to intercept the binding between OPs and endogenous AChE, thereby reducing the severity of OP poisoning. Through the coating of cellular membranes, polymeric nanoparticles were successfully functionalized with enzymatically active membrane-bound proteins. The RBC-NPs demonstrated herein largely retained the content and functions of AChE on natural RBCs. These biomimetic nanoparticles were previously demonstrated to possess numerous cell-like functionalities, including long systemic circulation (16) and spontaneous interactions with membrane-active pathogenic factors (15, 18). The present study validates the potential of RBC-NPs as a novel form of anti-OP bioscavenger. The therapeutic potential of RBC-NPs was demonstrated using mouse models of OP poisoning via both intravenous and oral OP challenges. It was shown that the mortality rate was sharply reduced after treatment of RBC-NPs. In contrast, equivalent doses of PEG-NPs of analogous physicochemical properties failed to improve the survival rate of the DDVP-challenged mice, thereby reaffirming the unique functionality of RBC-NPs in anti-OP applications. Unlike existing anti-OP therapies that compete with ACh or block ACh receptors, the RBC-NPs function as an OP decoy and are thus less likely to induce anticholinergic side effects including ventricular fibrillation, dizziness, nausea, blurred vision, loss of balance, dilated pupils, photophobia, dry mouth, and extreme confusion. The entirely biocompatible and biodegradable nature of the platform also minimizes safety concerns associated with nanomaterials administration.

Toward future translation, the RBC-NP platform may present production advantages over other experimental bioscavenger platforms as purified RBCs are readily available in blood transfusion practices. It can be envisioned blood-type matched RBC-NPs may be administered to poisoned subjects for OP neutralization with minimal concerns of immunogenicity. In addition, as both nucleated and non-nucleated mammalian cell membranes have been demonstrated for the preparation of cell-membrane cloaked nanoparticles (16, 34), other biomimetic nanoparticles with specific surface receptors may be prepared for different biodetoxification purposes. The unique bioscavenger approach using cell-membrane cloaked nanoparticles provides novel strategies in removing biological and chemical toxicants.

Materials and Methods

Ethics Statement

All animal experiments followed protocols that were reviewed, approved and performed under the regulatory supervision of the University of California, San Diego's institutional biosafety program and the Institutional Animal Care and Use Committee (IACUC).

Preparation of RBC-NPs and Characterization.

RBC-NPs were prepared as previously described (19). Briefly, 100 nm PLGA polymeric cores were prepared by a nanoprecipitation method. Firstly, 0.67 dL/g carboxy-terminated 50:50 PLGA (LACTEL Absorbable Polymers) was dissolved in acetone at a concentration of 10 mg/mL. One mL of the PLGA solution was added rapidly to 2 mL of water and then placed in a vacuum to accelerate acetone evaporation. The resulting nanoparticle solution was mixed with CD-1 mouse RBC membrane vesicles and sonicated for 2 min using an FS30D bath sonicator at a power of 100 W. The fluorescence-labeled RBC-NPs were prepared using the same method except that 1,1'-dioctadecyl-3,3,3',3'-tetramethylindodicarbocyanine perchlorate (DiD; excitation/emission=644/665 nm; Life Technologies) was incorporated into the polymer solution at a concentration of 10 μg/mL during the nanoparticle core preparation. Note that all stated concentration values for RBC-NPs refers to the concentration of the PLGA polymer in the nanoparticle formulation. The RBC-NP/DDVP complex was prepared by mixing 100 μL of RBC-NPs (5 mg/mL) with 10 μL of DDVP (1 mg/mL) for 15 min. Particle size and zeta potential of RBC-NPs and RBC-NP/DDVP complex were determined by dynamic light scattering (DLS) measurements using a Malvern ZEN 3600 Zetasizer, which showed an average hydrodynamic diameter of 123 nm and 130 nm, respectively. The morphology of the RBC-NP/DDVP was examined with transmission electron microscopy (TEM) after staining with 1 wt % uranyl acetate (16). As a control, DSPE-PEG(2000)-coated lipid-PLGA hybrid nanoparticles (PEG-NPs) were prepared through a nanoprecipitation method following a previously published protocol (35). As another control, PEGylated liposomes (PEG liposomes) consisting of 80 wt % of egg PC and 20 wt % of DSPE-PEG(2000)-methoxy (Avanti Polar Lipids) were prepared by a film hydration method as previously described (36). Measured by DLS, the diameters of the PEG-NPs and PEG-liposomes were 117 nm and 105 nm, respectively.

Western Blotting of AChE and AChE Activity in RBC-NPs.

RBC ghosts and RBC-NPs were prepared in SDS sample buffer (Invitrogen) and the total protein content in the samples was quantified by a Pierce BCA protein assay kit (Thermo). The samples were then resolved on a NuPAGE Novex 4-12% Bis-Tris 12-well gel in MOPS running buffer using Novex SureLock X-cell Electrophoresis System (Invitrogen). The samples were run at 165 V for 45 min. The proteins on the resulting polyacrylamide gel were then transferred to Protran pure nitrocellulose transfer and immobilization membrane (Perkin Elmer) at 15 V for 30 min. After blocking with 5% fresh milk in PBST for 2 h at room temperature, the nitrocellulose membrane was incubated with monoclonal mouse anti-AChE (1:2000 diluted in 5% fresh milk in PBST; Abgent) overnight at 4° C. After washing with PBST for 3 times, the nitrocellulose membrane was then incubated with goat anti-mouse IgG HRP conjugate (1:2000 diluted in 5% fresh milk in PBST; Millipore) for 2 h at room temperature. Afterwards, the stained nitrocellulose membrane was subjected to ECL western blotting substrate (Pierce) for 1 min and developed with a Mini-Medical/90 Developer (ImageWorks). Total blotting intensity was analyzed by ImageJ software to compare the AChE content between RBC-NPs and RBC ghosts. AChE activity in RBC-NPs and RBC ghosts was measured with an Amplex Red ACh/AChE assay kit (Invitrogen) using electric eel AChE as the standard.

DDVP Removal by RBC-NPs.

To investigate the DDVP absorption and removal capability of RBC-NPs, 100 μL of PBS (1×, pH=7.2) solution containing 4 mg/mL or 1 mg/mL of RBC-NPs was incubated with 10 μL of different concentrations of DDVP for 30 min Each sample was then spun down at 14,000 rpm in a Beckman Coulter Microfuge 22R Centrifuge for 10 min to pellet the nanoparticles. The free DDVP content in the supernatant was determined by using an HPLC system (Agilent 1100) with an analytical column (150 mm×4.6 mm; pore size 5 μm; ZORBAX SB-C18; Agilent) at room temperature. The mobile phase consisted of a mixture of acetonitrile and water (50:50, v/v) at a flow rate of 1.0 mL/min. The sample injection volume was 10 μL, and the detector wavelength was 215 nm. The DDVP removal was calculated with the formula: DDVP removal (%)=(1−DDVP in supernatant/total DDVP input)×100%. All experiments were performed in triplicate. DDVP removal was plotted and fitted with the binding-saturation equation in GraphPad Prism. To investigate the effect of RBC-NP concentration on DDVP removal, 10 μL of PBS (1×, pH=7.2) solution containing 5 μg DDVP was incubated with 100 μL of solution containing different concentrations of RBC-NPs for 30 min. Each sample was treated as described above and DDVP removal was calculated, plotted with DDVP concentration and fitted with the binding-saturation equation. To compare the removal capability of different nanoformulations, 100 μL of PBS (1×, pH=7.2) solution containing 4 mg/mL of RBC-NPs, PEG-NPs or PEG-liposomes was incubated with 10 μL of solution containing 5 μg DDVP for 30 min. Each sample was processed and analyzed as described above and the DDVP removal was calculated.

In Vitro Anti-OP Effect by RBC-NPs.

In vitro anti-OP effect by RBC-NPs was investigated based on the AChE activity on RBC ghosts following co-incubation with RBC-NPs and DDVP. Briefly, 100 μL of PBS (1×, pH=7.2) solution containing 2 μL of RBC ghosts and different concentrations of RBC-NPs was incubated with different concentrations of DDVP for 30 min. Each sample then was centrifuged at 2,000 rpm in a Beckman Coulter Microfuge 22R Centrifuge for 10 min to selectively spin down the RBC ghosts, leaving RBC-NPs and DDVP in the supernatant. After discarding the supernatant, the pellet of RBC ghosts was suspended in 10 μL of PBS and their AChE activity was measured by an Amplex Red ACh/AChE assay kit (Invitrogen). To compare the AChE protection effect by different nanoformulations, 100 μL of PBS (1×, pH=7.2) solution containing 4 mg/mL of RBC-NPs, PEG-NPs or PEG-liposomes was incubated with 10 μL of solution containing 5 μg DDVP for 30 min. Each sample was spun down at 14,000 rpm in a Beckman Coulter Microfuge 22R Centrifuge for 10 min to remove the nanoformulations. The supernatant was added to 2 μL of RBC ghosts and incubated for 30 min. AchE activity on the isolated RBC ghosts was measured as described above.

In Vivo OP Detoxification by RBC-NPs Following Intravenous DDVP Challenge.

RBC-NPs and PEG-NPs at a concentration 25 mg/mL suspended in 10% sucrose were first prepared. Thirty (30) CD-1 mice were randomized to three groups of 10 mice. Each group of mice was intravenously administered with DDVP at a dose of 10 mg/kg through the tail vein. The treatment group received a tail vein intravenous injection of 200 mg/kg of nanoformulation immediately following the DDVP injection. The no treatment group was injected with DDVP only. Survival after DDVP injection was recorded and statistical significance was determined using the log-rank test. For the no treatment group and the PEG-NP group, 50 μL of blood was collected by cardiac puncture immediately after death. For the RBC-NP group, 50 μL of blood was collected 1 h after DDVP injection by submandibular puncture. RBC ghosts were then derived from the collected blood based on a previously described protocol (16) and the AChE activity of 10 μL of RBC ghosts was measured and compared to that of normal mice.

In Vivo OP Detoxification by RBC-NPs Following Oral Administration of DDVP.

RBC-NPs and PEG-NPs at a concentration 25 mg/mL suspended in 10% sucrose were first prepared. Thirty (30) CD-1 mice were placed into three groups of 10 mice. Each group of mice was orally administered with DDVP at a dose of 150 mg/kg. The treatment group received a tail vein intravenous injection of 200 mg/kg of nanoformulation immediately after DDVP administration. The no treatment group was administered with DDVP only. Survival after DDVP administration was recorded and statistical significance was determined using the log-rank test. For the no treatment group and the PEG-NP group, 50 µL of blood was collected by cardiac puncture immediately after death. For the RBC-NP group, 50 µL of blood was collected 1 h after DDVP administration by submandibular puncture. RBC ghosts were derived as previously described (16) and the AChE activity of 10 µL of RBC ghosts was measured to compare with that of normal mice.

RBC AChE Activity Recovery after RBC-NP Treatment.

After mice were challenged by intravenous or oral DDVP administration and treated with RBC-NPs, 50 µL of blood was collected on day 0, day 2, and day 4. RBC ghosts were derived from the collected blood and the AChE activity of 10 µL of RBC ghosts was measured to monitor the recovery of AChE activity following RBC-NP treatment.

Biodistribution of the RBC-NP/DDVP Complex.

RBC-NP/DDVP complex was first prepared by mixing 5 mg of DiD-labeled RBC-NPs with 250 µg of DDVP. The mixture was subsequently filtered through a Sepharose CL-4B column to remove unbound DDVP. For the biodistribution study, 6 week-old male CD-1 mice were sacrificed 24 h after intravenous injection of the fluorescent RBC-NP/DDVP complex via the tail vein. The heart, liver, spleen, kidneys, lung, brain and blood were collected and homogenized. The fluorescence of the homogenate at 665 nm with an excitation wavelength of 640 nm was read using a Tecan Infinite M200 Multiplate Reader. The resulting signal was then multiplied by the corresponding organ weight to obtain the total organ fluorescence and the relative distribution of the RBC-NP/DDVP complex in each organ was calculated (n=6). For the hepatotoxicity study, one group of mice was sacrificed on day 3 following the injection of the RBC-NP/DDVP complex and another group was sacrificed on day 7. The livers were collected, sectioned, and stained with H&E for histological analyses.

REFERENCES

1. D. Gunnell, M. Eddleston, M. R. Phillips, F. Konradsen, The global distribution of fatal pesticide self-poisoning: Systematic review. *BMC Public Health* 7, 357 (2007).
2. M. Eddleston et al., Epidemiology of intentional self-poisoning in rural Sri Lanka. *Br. J. Psychiatry* 187, 583-584 (2005).
3. R. C. Gupta, Handbook of toxicology of chemical warfare agents. Elsevier, UK, (2009).
4. N. Yanagisawa, H. Morita, T. Nakajima, Sarin experiences in Japan: Acute toxicity and long-term effects. *J. Neurol. Sci.* 249, 76-85 (2006).
5. P. W. Elsinghorst, F. Worek, H. Thiermann, T. Wille, Drug development for the management of organophosphorus poisoning. *Expert Opin. Drug. Discov.* 8, 1467-1477 (2013).
6. M. Jokanovic, M. Prostran, Pyridinium oximes as cholinesterase reactivators. Structure-activity relationship and efficacy in the treatment of poisoning with organophosphorus compounds. *Curr. Med. Chem.* 16, 2177-2188 (2009).
7. M. Balali-Mood, M. Shariat, Treatment of organophosphate poisoning. Experience of nerve agents and acute pesticide poisoning on the effects of oximes. *J. Physiol. Paris* 92, 375-378 (1998).
8. R. Rahimi, S. Nikfar, M. Abdollahi, Increased morbidity and mortality in acute human organophosphate-poisoned patients treated by oximes: A meta-analysis of clinical trials. *Hum. Exp. Toxicol.* 25, 157-162 (2006).
9. A. Karakus et al., Cases of organophosphate poisoning treated with high-dose of atropine in an intensive care unit and the novel treatment approaches. *Toxicol. Ind. Health* 30, 421-425 (2012).
10. F. Nachon, X. Brazzolotto, M. Trovaslet, P. Masson, Progress in the development of enzyme-based nerve agent bioscavengers. *Chem. Biol. Interact.* 206, 536-544 (2013).
11. J. J. Ceron, F. Tecles, A. Tvarijonaviciute, Serum paraoxonase 1 (PON1) measurement: An update. *BMC Vet. Res.* 10, 74 (2014).
12. D. Rochu, E. Chabriere, P. Masson, Human paraoxonase: A promising approach for pre-treatment and therapy of organophosphorus poisoning. *Toxicology* 233, 47-59 (2007).
13. B. P. Doctor, A. Saxena, Bioscavengers for the protection of humans against organophosphate toxicity. *Chem. Biol. Interact.* 157-158, 167-171 (2005).
14. F. Worek, M. Koller, H. Thiermann, L. Szinicz, Diagnostic aspects of organophosphate poisoning. *Toxicology* 214, 182-189 (2005).
15. C. M. Hu, R. H. Fang, J. Copp, B. T. Luk, L. Zhang, A biomimetic nanosponge that absorbs pore-forming toxins. *Nat. Nanotechnol.* 8, 336-340 (2013).
16. C. M. Hu, L. Zhang, S. Aryal, C. Cheung, R. H. Fang, Erythrocyte membrane-camouflaged polymeric nanoparticles as a biomimetic delivery platform. *Proc. Natl. Acad. Sci. U.S.A* 108, 10980-10985 (2011).
17. C. M. Hu, R. H. Fang, B. T. Luk, L. Zhang, Nanoparticle-detained toxins for safe and effective vaccination. *Nat. Nanotechnol.* 8, 933-938 (2013).
18. J. A. Copp et al., Clearance of pathological antibodies using biomimetic nanoparticles. *Proc. Natl. Acad. Sci. U.S.A* 111, 13481-13486 (2014).
19. C. M. Hu et al., 'Marker-of-self' functionalization of nanoscale particles through a top-down cellular membrane coating approach. *Nanoscale* 5, 2664-2668 (2013).
20. H. Hrabetz et al., Organophosphate poisoning in the developed world—a single centre experience from here to the millennium. *Chem. Biol. Interact.* 206, 561-568 (2013).
21. P. Masson, Evolution of and perspectives on therapeutic approaches to nerve agent poisoning. *Toxicol. Lett.* 206, 5-13 (2011).
22. M. Eddleston et al., Speed of initial atropinisation in significant organophosphorus pesticide poisoning—A systematic comparison of recommended regimens. *J. Toxicol. Clin. Toxicol.* 42, 865-875 (2004).
23. H. Thiermann, F. Worek, K. Kehe, Limitations and challenges in treatment of acute chemical warfare agent poisoning. *Chem. Biol. Interact.* 206, 435-443 (2013).
24. J. Kassa, K. Musilek, J. Z. Karasova, K. Kuca, J. Bajgar, Two possibilities how to increase the efficacy of antidotal treatment of nerve agent poisonings. *Mini Rev. Med. Chem.* 12, 24-34 (2012).
25. P. Masson, D. Rochu, Catalytic bioscavengers against toxic esters, an alternative approach for prophylaxis and treatments of poisonings. *Acta Naturae* 1, 68-79 (2009).
26. M. Valiyaveettil et al., Protective efficacy of catalytic bioscavenger, paraoxonase 1 against sarin and soman exposure in guinea pigs. *Biochem. Pharmacol.* 81, 800-809 (2011).

27. M. Valiyaveettil, Y. A. Alamneh, B. P. Doctor, M. P. Nambiar, Crossroads in the evaluation of paraoxonase 1 for protection against nerve agent and organophosphate toxicity. *Toxicol. Lett.* 210, 87-94 (2012).
28. Y. Ashani, S. Pistinner, Estimation of the upper limit of human butyrylcholinesterase dose required for protection against organophosphates toxicity: A mathematically based toxicokinetic model. *Toxicol. Sci.* 77, 358-367 (2004).
29. A. Saxena, W. Sun, J. M. Fedorko, I. Koplovitz, B. P. Doctor, Prophylaxis with human serum butyrylcholinesterase protects guinea pigs exposed to multiple lethal doses of soman or VX. *Biochem. Pharmacol.* 81, 164-169 (2011).
30. O. Cohen et al., Comparison of polyethylene glycol-conjugated recombinant human acetylcholinesterase and serum human butyrylcholinesterase as bioscavengers of organophosphate compounds. *Mol. Pharmacol.* 70, 1121-1131 (2006).
31. M. Wandhammer et al., Structural study of the complex stereoselectivity of human butyrylcholinesterase for the neurotoxic V-agents. *J. Biol. Chem.* 286, 16783-16789 (2011).
32. B. D. Henry et al., Engineered liposomes sequester bacterial exotoxins and protect from severe invasive infections in mice. *Nat. Biotechnol.* 33, 81-88 (2014).
33. J. C. Leroux, Injectable nanocarriers for biodetoxification. *Nat. Nanotechnol.* 2, 679-684 (2007).
34. R. H. Fang et al., Cancer cell membrane-coated nanoparticles for anticancer vaccination and drug delivery. *Nano Lett.* 14, 2181-2188 (2014).
35. L. Zhang et al., Self-assembled lipid-polymer hybrid nanoparticles: A robust drug delivery platform. *ACS Nano* 2, 1696-1702 (2008).
36. D. Yang et al., The antimicrobial activity of liposomal lauric acids against *Propionibacterium acnes*. *Biomaterials* 30, 6035-6040 (2009).

The invention claimed is:

1. A method for decreasing or neutralizing the effect of a toxin in a subject, which method comprises administering, to a subject in need, or to cells of said subject, an effective amount of a nanoparticle comprising a) an inner core comprising a non-cellular material, and b) an outer surface comprising a plasma membrane derived from a source red blood cell, wherein said toxin is dichlorvos (DDVP).

2. The method of claim 1, which is used for decreasing the effect of a toxin in a subject.

3. The method of claim 1, wherein the inner core comprises a polymeric particle core.

4. The method of claim 1, wherein the inner core comprises a biocompatible or a synthetic material selected from the group consisting of poly(lactic-c-glycolic acid) (PLGA), polylactic acid (PLA), polyglycolic acid (PGA), polycaprolactone (PCL), polylysine, and polyglutamic acid.

5. The method of claim 1, wherein the inner core supports the outer surface.

6. The method of claim 1, wherein the nanoparticle further comprises a releasable cargo.

7. The method of claim 1, wherein the nanoparticle substantially lacks constituents of the source red blood cell that are not plasma membrane of the source red blood cell.

8. The method of claim 1, wherein the nanoparticle substantially maintains natural structural integrity or activity of the plasma membrane derived from the source red blood cell.

9. The method of claim 1, wherein the nanoparticle is biocompatible or biodegradable.

10. The method of claim 1, wherein the inner core of the nanoparticle comprises PLGA.

11. The method of claim 1, wherein the nanoparticle substantially lacks immunogenicity to the subject.

12. The method of claim 11, wherein the red blood cell plasma membrane is derived from a source red blood cell from the same species as the subject.

13. The method of claim 1, wherein the toxin binds to a target cell of the subject and to the source red blood cell via the same mechanism.

14. The method of claim 1, wherein the toxin binds to a target cell of the subject and the source red blood cell via different mechanisms.

15. The method of claim 1, which further comprises assessing efficacy of the nanoparticle and/or the another active ingredient in decreasing or neutralizing the effect of a toxin in the subject.

16. The method of claim 1, which is used to decrease or neutralize the effect of the toxin in a subject by at least 10% compared to a comparable untreated subject or to the same subject at an untreated stage.

17. The method of claim 1, wherein red blood cell acetylcholinesterase activity in the treated subject returns to normal after treatment.

* * * * *